(12) United States Patent
Uehara et al.

(10) Patent No.: US 10,864,145 B2
(45) Date of Patent: Dec. 15, 2020

(54) MALE CONNECTOR

(71) Applicant: JMS CO., LTD., Hiroshima (JP)

(72) Inventors: Yasumasa Uehara, Hiroshima (JP);
Yutaka Ueda, Hiroshima (JP);
Kazuhiko Takimoto, Hiroshima (JP);
Megumi Harada, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 14 days.

(21) Appl. No.: 15/103,141

(22) PCT Filed: Dec. 9, 2014

(86) PCT No.: PCT/JP2014/082565
§ 371 (c)(1),
(2) Date: Jun. 9, 2016

(87) PCT Pub. No.: WO2015/087880
PCT Pub. Date: Jun. 18, 2015

(65) Prior Publication Data
US 2016/0354288 A1    Dec. 8, 2016

(30) Foreign Application Priority Data

Dec. 11, 2013 (JP) ................................. 2013-256269

(51) Int. Cl.
*A61J 15/00* (2006.01)
*A61M 39/10* (2006.01)
*A61M 39/12* (2006.01)

(52) U.S. Cl.
CPC .......... *A61J 15/0026* (2013.01); *A61J 15/00* (2013.01); *A61M 39/1011* (2013.01);
(Continued)

(58) Field of Classification Search
CPC .... A61J 15/0026; A61J 15/00; A61J 15/0011; A61M 39/1011; A61M 39/1055;
(Continued)

(56) References Cited

U.S. PATENT DOCUMENTS 4,639,019 A * 1/1987 Mittleman ............ A61M 39/00
285/332
5,047,021 A * 9/1991 Utterberg .............. A61M 39/10
285/332
(Continued)

FOREIGN PATENT DOCUMENTS

CN      2579415 Y     10/2003
DE      43 18 101     12/1994
(Continued)

OTHER PUBLICATIONS

International Search Report for PCT/JP2014/082565, dated Mar. 3, 2015, 2 pages.
(Continued)

*Primary Examiner* — Kevin C Sirmons
*Assistant Examiner* — Tezita Z Watts
(74) *Attorney, Agent, or Firm* — Hamre, Schumann, Mueller & Larson, P.C.

(57) ABSTRACT

A male connector (1) includes a luer portion (10) connected to the upstream end of a tube (8) used in enteral feeding, and a lock portion (20) that is removably attached to the luer portion. The luer portion (10) includes a tubular male luer (11) in which a channel (17) in communication with the tube (8) is formed. The lock portion (20) has a hollow tubular shape and is open at two ends, and includes female threading (21) that opposes the male luer on the inner circumferential face of the lock portion (20). The male luer (11) is inserted into the lock portion (20). Rotation prevention mechanisms (16, 26) that engage with one another are provided on the
(Continued)

luer portion (10) and the lock portion (20) such that the lock portion (20) does not rotate relative to the luer portion (10).

12 Claims, 34 Drawing Sheets

(52) U.S. Cl.
CPC ........ *A61M 39/1055* (2013.01); *A61M 39/12* (2013.01); *A61M 2039/1033* (2013.01)

(58) Field of Classification Search
CPC .......... A61M 2039/1033; A61M 39/12; A61M 2039/1044; A61M 2039/1027; A61M 2039/1038
See application file for complete search history.

(56) References Cited

U.S. PATENT DOCUMENTS

| | | | | |
|---|---|---|---|---|
| 5,395,348 A | * | 3/1995 | Ryan | A61M 39/14 604/247 |
| 5,702,374 A | | 12/1997 | Johnson | |
| 7,396,051 B2 | * | 7/2008 | Baldwin | A61M 39/26 285/354 |
| 8,585,099 B2 | * | 11/2013 | Nielson | F16L 33/24 285/247 |
| 2003/0184090 A1 | | 10/2003 | Guala | |
| 2005/0251102 A1 | * | 11/2005 | Hegland | A61M 39/12 604/500 |
| 2008/0140055 A1 | * | 6/2008 | Shirley | A61M 39/1011 604/535 |
| 2009/0062775 A1 | | 3/2009 | Kitani | |
| 2010/0176584 A1 | | 7/2010 | Ito et al. | |
| 2012/0192968 A1 | * | 8/2012 | Bonnal | A61M 39/1011 137/454.2 |

FOREIGN PATENT DOCUMENTS

| | | |
|---|---|---|
| EP | 1 894 597 | 3/2008 |
| EP | 1 946 792 | 7/2008 |
| JP | 2005-000466 | 1/2005 |
| JP | 2012-081082 | 4/2012 |
| WO | 2008152871 | 12/2008 |
| WO | 2012/139949 | 10/2012 |

OTHER PUBLICATIONS

Supplemental European Search Report issued in corresponding European patent application, dated Jul. 13, 2017, 6 pages.

* cited by examiner

MALE CONNECTOR

TECHNICAL FIELD

The present invention relates to a male connector provided at the upstream end of a tube used in enteral feeding.

BACKGROUND ART

Enteral feeding is known as a method for administering nutrition and drugs to a patient without relying on oral administration. In enteral feeding, liquids such as nutrients, liquid food, and drugs (generally called "enteral nutrients") are administered to a patient via a transnasal catheter that has been inserted through the patient's nasal cavity and into their stomach or duodenum, or via a PEG (Percutaneous Endoscopic Gastrostomy) catheter that has been inserted into a gastrostomy formed in the patient's abdomen. The liquid to be administered to the patient is stored in a container. A bendable tube (referred to hereinafter as a "container-side tube") is connected to the outlet port of the container. The downstream end of the container-side tube is connected to the upstream end of a catheter that has been inserted into the patient (transnasal catheter, PEG catheter, or the like), or the upstream end of a bendable tube that is connected to the catheter (collectively referred to hereinafter as a "patient-side tube"). In general, a connector tool made up of a male connector and a female connector is used to connect the container-side tube and the patient-side tube. Conventionally, the male connector is provided at the downstream end of the container-side tube, and the female connector is provided at the upstream end of the patient-side tube (e.g., see Patent Document 1).

If the liquid administered in enteral feeding is a liquid that has a low viscosity, problems occur, such as the liquid flowing backwards from the stomach to the esophagus and developing into pneumonia, or the patient suffering from diarrhea caused by moisture in the liquid not being sufficiently absorbed in the body. In view of this, in enteral feeding, the liquid is often given a higher viscosity (i.e., semi-solidified) by the addition of a thickening agent or a thickener, for example. Such a liquid that has been given a higher viscosity has a low fluidity, and thus has a high resistance when passing through a tube. Accordingly, when a liquid that has been given a higher viscosity is administered to a patient, pressure is applied to the liquid to pressure-feed it.

For this reason, there is desire for the connector tool that connects the container-side tube and the patient-side tube to include lock mechanisms that engage with each other in order to be able to withstand the pressure applied to the liquid. In view of this, international standard ISO 80369-3 regarding nutrition-related medical equipment has been given consideration for the international standardization of male connectors and female connectors for use in such applications.

As shown in FIGS. 11A and 11B, a male connector 910 under consideration as ISO 80369-3 has a tubular male luer 911 and an outer tube 913 that surrounds the male luer 911. An outer circumferential face 912 of the male luer 911 is a tapered face whose outer diameter decreases as it approaches the tip (a so-called male tapered face). A channel 917 that passes through the male luer 911 along the lengthwise direction thereof is formed in the male luer 911. Female threading 915 is formed in the inner circumferential face of the outer tube 913 that opposes the male luer 911.

On the other hand, as shown in FIGS. 12A and 12B, a female connector 920 under consideration as ISO 80369-3 has a cylindrical insertion portion (female luer) 921 into which the male luer 911 is inserted. An inner circumferential face 922 of the insertion portion 921 is a tapered face whose inner diameter increases as it approaches the tip (a so-called female tapered face). Male threading 925 is formed on the outer circumferential face of the insertion portion 921.

The male connector 910 and the female connector 920 are connected by inserting the male luer 911 into the insertion portion 921 and screwing the female threading 915 and the male threading 925 together. Since the outer circumferential face 912 of the male luer 911 and the inner circumferential face 922 of the insertion portion 921 are tapered faces that have the same taper angle, they come into liquid-tight surface contact with each other. The female threading 915 and the male threading 925 that are screwed together constitute lock mechanisms for locking the connected state of the male connector 910 and the female connector 920. The male connector 910 and female connector 920 provide a connection having excellent liquid-tightness (property of preventing the leakage of a liquid from the connection portion of the male connector and the female connector even if pressure is applied to the liquid) and excellent connection strength (property of preventing separation of the connected male connector and female connector even if pulling force is applied).

In the international standard ISO 80369-3, consideration has been given to providing the male connector 910 at the upstream end of the patient-side tube and providing the female connector 920 at the downstream end of the container-side tube in order to prevent mistaken connection with a connector used in a field other than enteral nutrition.

PRIOR ART DOCUMENTS

Patent Document

[Patent Document 1] WO 2008/152871

DISCLOSURE OF INVENTION

Problem to be Solved by the Invention

In the male connector 910, the outer tube 913 surrounds the male luer 911, and the female threading 915 is formed in the inner circumferential face of the outer tube 913. Accordingly, enteral nutrients easily become stuck in the gap between the male luer 911 and the outer tube 913, and in the valley of the female threading 915 in particular. Once an enteral nutrient becomes stuck in the valley of the female threading 915, it is difficult to wipe away that enteral nutrient. If an enteral nutrient becomes stuck for a long period of time, the male connector 910 can become unsanitary. Eventually, it is possible that bacteria will breed in the male connector 910, enter the patient's body, and cause a serious complication.

If the patient-side tube provided with the male connector 910 is the catheter inserted into the patient, the male connector 910 remains indwelled along with the catheter in the patient. In the case of a PEG catheter, the catheter is normally replaced every 1 to 3 months. Contamination of the male connector increases the frequency of catheter replacement.

An object of the present invention is to provide a male connector that includes female threading that surrounds a male luer, and that can be easily maintained in a sanitary state.

Means for Solving Problem

A male connector according to an aspect of the present invention is a male connector provided at an upstream end of a tube used in enteral feeding, the male connector including a luer portion connected to the tube and a lock portion that is removably attached to the luer portion. The luer portion includes a tubular male luer in which a channel in communication with the tube is formed. The lock portion has a hollow tubular shape and is open at two ends, and includes female threading that opposes the male luer on an inner circumferential face of the lock portion. The male luer is inserted into the lock portion. Rotation prevention mechanisms that engage with one another are provided on the luer portion and the lock portion such that the lock portion does not rotate relative to the luer portion.

Effects of the Invention

In the male connector of the present invention, the lock portion provided with the female threading is removably attached to the luer portion provided with the male luer. Accordingly, it is possible to remove the lock portion from the luer portion and clean the luer portion and the lock portion separately. The lock portion can also be replaced with a new one. Accordingly, the male connector of the present invention can be easily maintained in a sanitary state.

The male connector includes rotation prevention mechanisms for preventing the lock portion from rotating relative to the luer portion. Accordingly, it is possible to reduce the possibility of the luer portion and the lock portion becoming separated unintentionally.

DESCRIPTION OF THE INVENTION

Figure 1A:
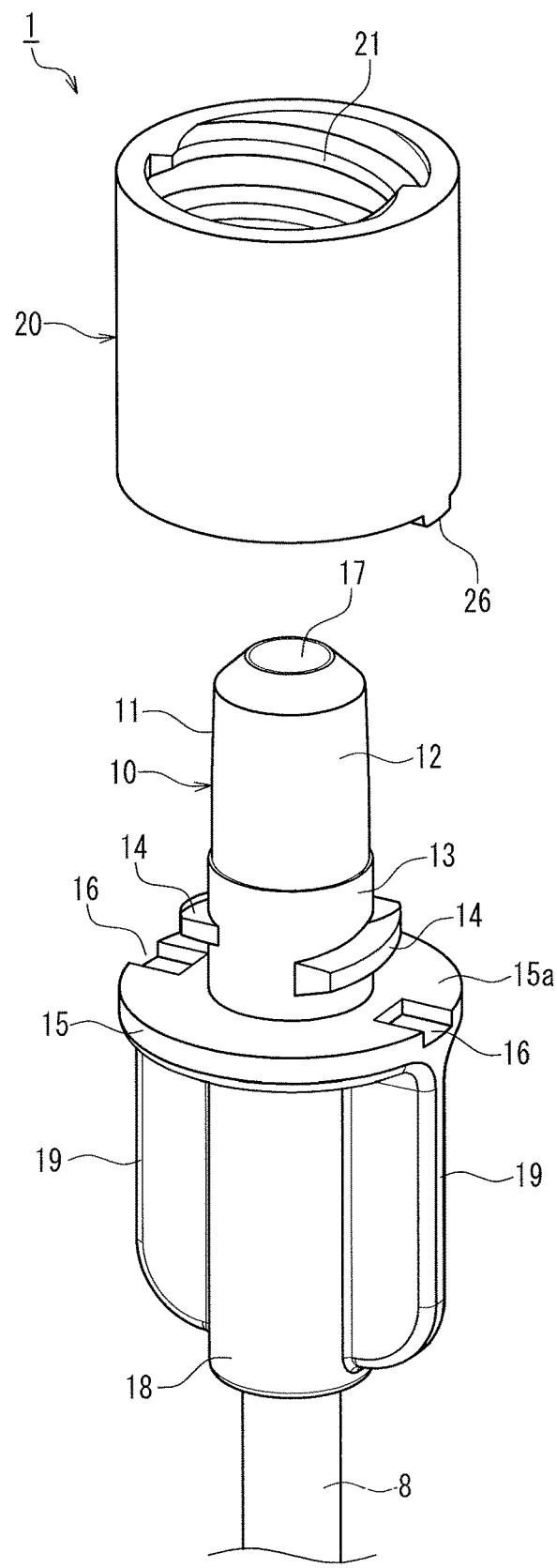
FIG. 1A is an exploded perspective view of a male connector according to Embodiment 1 of the present invention, as viewed from above.

In the above-described male connector of the present invention, it is preferable that the luer portion is made of a harder material than the lock portion. According to this configuration, there is a reduced possibility of the luer portion becoming damaged or worn, thus making it possible to extend the lifetime of the luer portion, which is not easily replaced due to being provided on the tube. This is advantageous to reducing the frequency of replacement of the tube that is provided with the luer portion.

It is preferable that the rotation prevention mechanisms include a protruding portion provided on the lock portion and a receding portion that is provided in the luer portion, the protruding portion being fitted into the receding portion. The rotation prevention mechanisms are constituted by a protruding portion and a receding portion, thus making it possible to simplify the configuration of the rotation prevention mechanisms. A protruding portion that is relatively likely to become damaged and worn is provided on the lock portion, and a receding portion that is relatively unlikely to become damaged and worn is provided on the luer portion, thus making it possible to extend the lifetime of the luer portion, which is not easily replaced due to being provided on the tube. This is advantageous to reducing the frequency of replacement of the tube that is provided with the luer portion.

The rotation prevention mechanisms can include a protruding portion formed on one of the lock portion and the luer portion, and a receding portion formed on another one of the lock portion and the luer portion. The protruding portion may include an inclined face on one side in a circumferential direction, and include a vertical face on another side in the circumferential direction. In this case, it is preferable that the receding portion includes an inclined face and a vertical face that respectively oppose the inclined face and the vertical face of the protruding portion when the protruding portion is fitted into the receding portion. According to this configuration, it is possible to reduce the possibility of the luer portion and the lock portion becoming separated unintentionally, while the operation of attaching the lock portion to the luer portion is relatively easy.

It is preferable that the male connector can be connected to a female connector that includes an insertion portion for insertion of the male luer and male threading that is to be screwed together with the female threading. In this case, it is preferable that the rotation prevention mechanisms are configured such that when the luer portion and the female connector are rotated in mutually opposite directions in order to separate the male connector and the female connector that are connected to each other, screwing together of the female threading and the male threading is loosened, without the lock portion rotating relative to the luer portion. According to this configuration, when the luer portion and the female connector are respectively gripped and rotated in mutually opposite directions in order to separate the male connector and the female connector, it is possible to reliably loosen the screwing together of the female threading and the male threading.

It is preferable that the separation prevention mechanisms that engage with one another are provided on the luer portion and the lock portion such that the luer portion and the lock portion do not become separated along a lengthwise direction of the male luer. According to this configuration, the male connector of the present invention and a female connector can be connected with excellent liquid-tightness and excellent connection strength.

It is preferable that the separation prevention mechanisms include screwing structures. According to this configuration, a firm connection between the luer portion and the lock portion, and the ability to easily connect/separate the luer portion and the lock portion can both be achieved with a simple structure.

The luer portion may include a base end portion on which the male luer is provided. Also, the lock portion may include an extension portion arranged outward of the base end portion. In this case, it is preferable that the extension portion is configured such that rotation torque can be applied to the male connector via the extension portion. According to this configuration, rotation torque applied to the extension portion is transmitted to the female threading without passing through the rotation prevention mechanisms. Accordingly, even in the case where the male connector and the female connector have been screwed together firmly, it is possible to loosen the screwing together thereof by applying a large amount of rotation torque to the extension portion.

The extension portion can include at least one bar-shaped member that extends parallel with a lengthwise direction of the luer portion. The at least one bar-shaped member is arranged so as to protrude outward from an outer circumferential face of the base end portion. According to this configuration, an extension portion to which rotation torque can be applied can be configured with a simple configuration. Also, due to the extension portion including at least one bar-shaped member, there is an improvement in the operability of connection to and separation from the female connector, and an improvement in the operability of cleaning the female threading of the lock portion.

It is preferable that a liquid-tight seal between the luer portion and the lock portion is formed at a position on a tube side relative to the male luer. According to this configuration, it is possible to prevent a nutrient from leaking out from between the luer portion and the lock portion.

It is preferable that the liquid-tight seal is formed by fitting together of a male tapered face formed on the luer portion and a female tapered face formed on the lock portion. According to this configuration, the liquid-tight seal can be formed with a simple configuration. Also, the liquid-tight seal can be formed by merely attaching the lock portion to the luer portion.

It is preferable that the male luer and the female threading are compliant with ISO 80369-3. According to this configuration, the male connector of the present invention and a female connector compliant with ISO 80369-3 can be connected with excellent liquid-tightness and excellent connection strength.

It is preferable that at least one of the luer portion and the lock portion includes a protrusion (convex portion) or recession (concave portion) for facilitating attachment and detachment of the lock portion to and from the luer portion. According to this configuration, there is an improvement in the operability of the attachment and separation of the lock portion to and from the luer portion. The protrusion or recession may be configured so as to be directly gripped by an operator, or may be configured so as to engage with a jig gripped by the operator.

The male connector of the present invention may further include a jig configured so as to engage with the protrusion or recession. In this case, it is preferable that the jig is configured such that rotation torque can be applied to the luer portion or the lock portion via the jig. According to this configuration, the attachment and separation of the lock portion to and from the luer portion can be performed easily.

Hereinafter, the present invention will be described in detail while disclosing preferred embodiments. Note that, it goes without saying that the present invention is not limited to the following embodiments. For the sake of convenience in the description, the drawings that are referenced in the following description show simplifications of, among the constituent members of the embodiments of the present invention, only relevant members that are necessary for describing the present invention. The present invention can therefore include arbitrary constituent members that are not shown in the following drawings. Also, the dimensions of the actual constituent members, the ratios of the dimensions of the members, and the like are not shown faithfully in the drawings referenced below.

Embodiment 1

Configuration

Figure 1B:
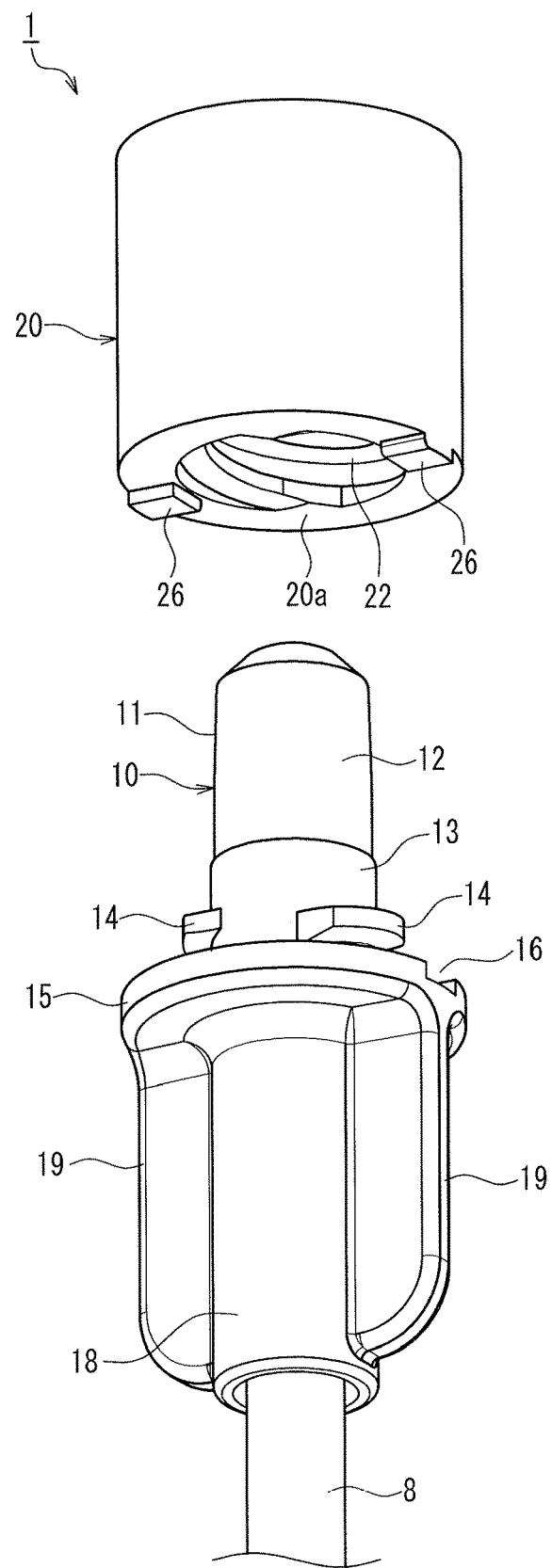
FIG. 1B is an exploded perspective view of the male connector according to Embodiment 1 of the present invention, as viewed from below.
Figure 1C:
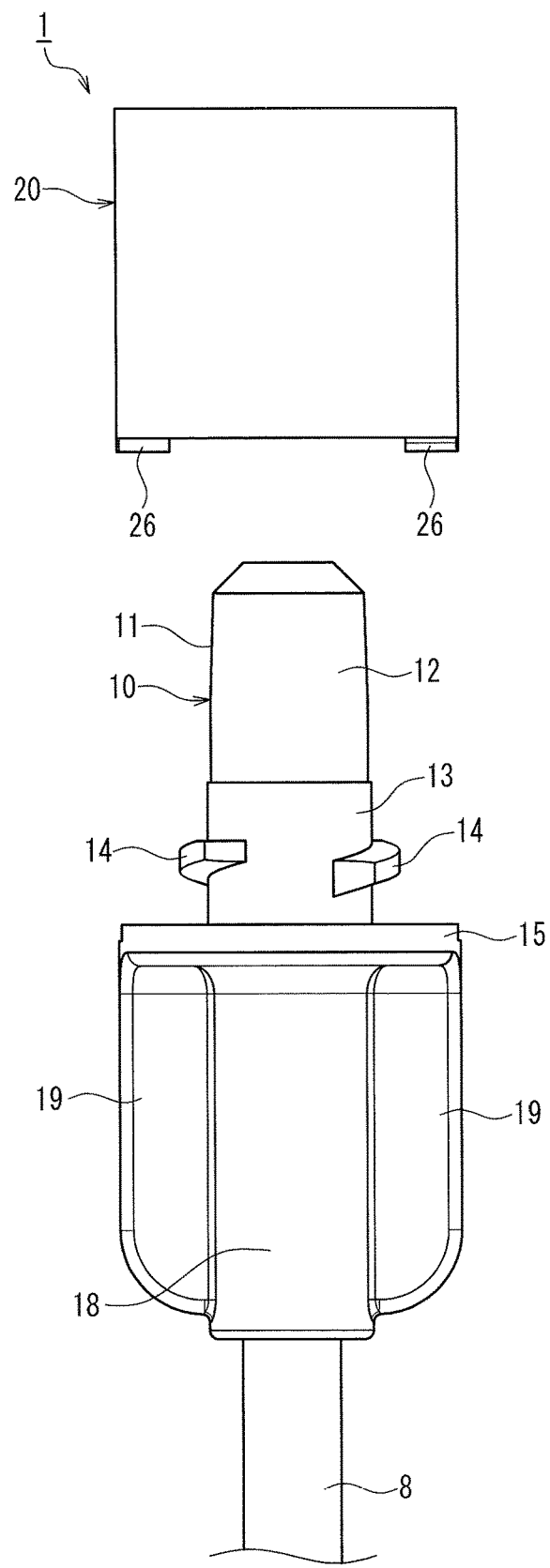
FIG. 1C is an exploded side view of the male connector according to Embodiment 1 of the present invention.
Figure 1D:
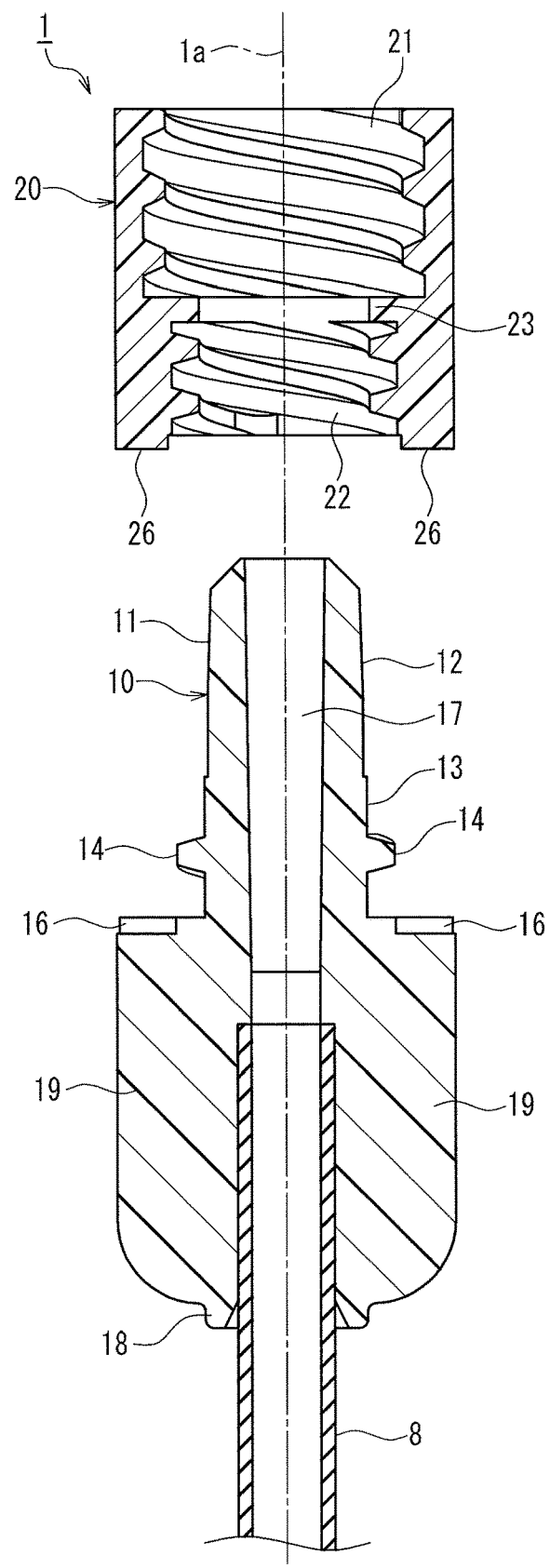
FIG. 1D is an exploded cross-sectional view taken along a plane that includes the central axis of the male connector according to Embodiment 1 of the present invention.

FIG. 1A is an exploded perspective view of a male connector 1 according to Embodiment 1 of the present invention, as viewed from above. FIG. 1B is an exploded perspective view of the male connector 1, as viewed from below. FIG. 1C is an exploded side view of the male connector 1. FIG. 1D is an exploded cross-sectional view taken along a plane that includes a central axis 1a of the male connector 1. For the sake of convenience in the following description, the "up-down direction" refers to the direction parallel to the central axis 1a, the "upper side" of the male connector 1 refers to the upper side of the paper surface in FIGS. 1A to 1D, and the "lower side" of the male connector 1 refers to the lower side of the paper surface in FIGS. 1A to 1D. Also, the "circumferential direction" refers to the direction of rotation about the central axis 1a, the "radial direction" refers to the direction orthogonal to the central axis 1a, and the "horizontal direction" refers to the direction perpendicular to the central axis 1a. Note that "up-down direction", "upper side", "lower side", and "horizontal direction" do not mean orientations during actual use of the male connector 1.

The male connector 1 includes a luer portion 10 and a lock portion 20.

The luer portion 10 includes a tubular male luer 11 at one end, and includes a base end portion 18 at the other end. A disc-shaped flange 15 protrudes outward along the radial direction at a position between the male luer 11 and the base end portion 18. One end of a flexible tube 8 is inserted into the base end portion 18 and fixed thereto. A channel 17 passes through the male luer 11 along the central axis 1a. The channel 17 is in communication with the tube 8.

An outer circumferential face 12 of the male luer 11 is a tapered face (conical face) whose outer diameter decreases as it approaches the tip. A tubular portion 13 is provided between the male luer 11 and the flange 15. The outer circumferential face of the tubular portion 13 is a cylindrical face whose outer diameter is constant in the central axis 1a direction. A spiral protrusion 14 protrudes from the outer circumferential face of the tubular portion 13. The spiral protrusion 14 is a so-called discontinuous thread, in which the thread ridge of the male threading is divided so as to be discontinuous in the circumferential direction.

A face (upper face) 15a of the flange 15 on the male luer 11 side is a flat face that is perpendicular to the central axis 1a. A pair of receding portions 16 are formed in the upper face 15a of the flange 15. The pair of receding portions 16 are in rotation symmetry (two-fold symmetry) about the central axis 1a.

A pair of thin plate-shaped protrusions 19 are provided on the outer circumferential face of the base end portion 18. The pair of protrusions 19 extend along one plane that includes the central axis 1a.

The lock portion 20 has a hollow, approximately cylindrical shape, and is open at the two ends in the up-down direction. As shown in FIG. 1D, in order from the top, first female threading 21 and second female threading 22 are formed in the inner circumferential face of the lock portion 20, and are adjacent in the central axis 1a direction. The spiral directions of the first female threading 21 and the second female threading 22 are the same (right-handed threading in the present embodiment), and the effective diameter of the first female threading 21 is larger than that of the second female threading 22.

As shown in FIG. 1B, a lower face 20a of the lock portion 20 is a flat surface that is perpendicular to the central axis 1a. A pair of protruding portions 26 protrude downward from the lower face 20a of the lock portion 20. The pair of protruding portions 26 are in rotation symmetry (two-fold symmetry) about the central axis 1a.

The luer portion 10 and the lock portion 20 are made of a material that is hard (a hard material) and has a mechanical strength (rigidity) to the extent of substantially not deforming under external force. Examples of resin materials that can be used as this hard material include polypropylene (PP), polycarbonate (PC), polyacetal (POM), polystyrene, polyamide, polyethylene, rigid polyvinyl chloride, and acrylonitrile butadiene styrene copolymer (ABS), but there are no limitations on the resin material. Among these materials, polypropylene (PP), polycarbonate (PC), polyacetal (POM), and acrylonitrile butadiene styrene copolymer (ABS) are preferable. The luer portion 10 and the lock portion 20 can each be formed in an integrated manner using injection molding or the like and the aforementioned resin materials. The materials constituting the luer portion 10 and the lock portion 20 may be the same or different from each other.

In the case where the luer portion 10 and the lock portion 20 are constituted by different materials, it is preferable that the luer portion 10 is made of a material that is relatively harder than that of the lock portion 20. For example, it is possible for the luer portion 10 to be constituted by ABS, and the lock portion 20 to be constituted by PP.

A bendable hollow tube can be used as the tube 8 that is connected to the luer portion 10. It is preferable that the tube 8 has a property of easily deforming under external force, and immediately returning to a default state when the external force disappears (so-called rubber-like elasticity). Although there are no limitations on the material of the tube 8, it is possible to use a soft material that has rubber-like elasticity (a so-called elastomer). For example, it is possible to use a rubber such as natural rubber, isoprene rubber, or silicone rubber; a thermoplastic elastomer such as styrene elastomer, olefin elastomer, or polyurethane elastomer; or soft polyvinyl chloride. Among these materials, silicone rubber is preferable. The tube 8 may be a catheter that is indwelled in the patient with the downstream end inserted into the patient (e.g., a transnasal catheter or a PEG catheter), or may be a tube that is connected to the upstream end of such a catheter. The method for fixing the luer portion 10 and the tube 8 may be any method, such as adhesion or welding, but there are no limitations on the fixing method.

The lock portion 20 can be repeatedly attached to and detached from the luer portion 10. The attachment of the lock portion 20 to the luer portion 10 is performed as described below.

As shown in FIGS. 1A to 1D, the luer portion 10 and the lock portion 20 are arranged so as to oppose each other. The male luer 11 is inserted into the lock portion 20 from the lower side thereof. The spiral protrusion 14 of the luer portion 10 collides with the thread ridge of the second female threading 22 of the lock portion 20. The lock portion 20 is rotated relative to the luer portion 10, thus screwing the spiral protrusion 14 and the second female threading 22 together. As the lock portion 20 is rotated, the male luer 11 and the tubular portion 13 advance inside the lock portion 20. The pair of protruding portions 26 of the lock portion 20 soon come into contact with the upper face 15a of the flange 15 of the luer portion 10, and slide thereon. Finally, the pair of protruding portions 26 are fitted into the pair of receding portions 16 of the luer portion 10, and, at the same time, the lower face 20a of the lock portion 20 and the upper face 15a of the flange 15 come into contact or approach each other. When the pair of protruding portions 26 are fitted into the pair of receding portions 16, the rotation torque for rotating the lock portion 20 changes, and the operator can feel that change as a clicking sensation through their fingers.

Figure 2A:
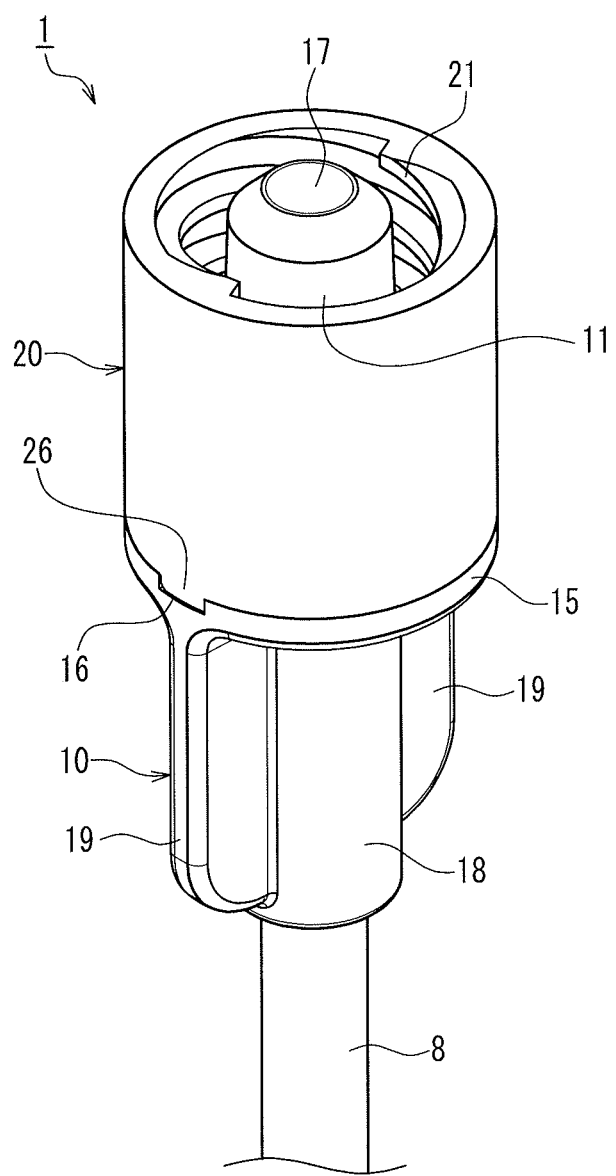
FIG. 2A is a perspective view of the male connector according to Embodiment 1 of the present invention, as viewed from above.
Figure 2B:
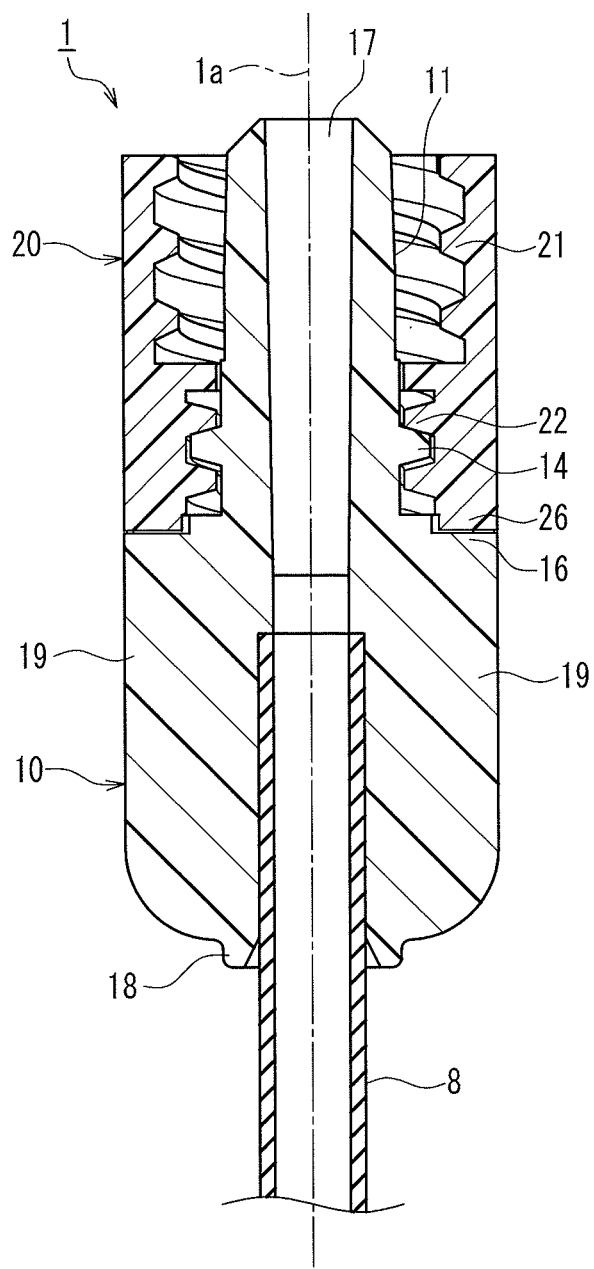
FIG. 2B is a cross-sectional view taken along a plane that includes the central axis of the male connector according to Embodiment 1 of the present invention.
Figure 11A:
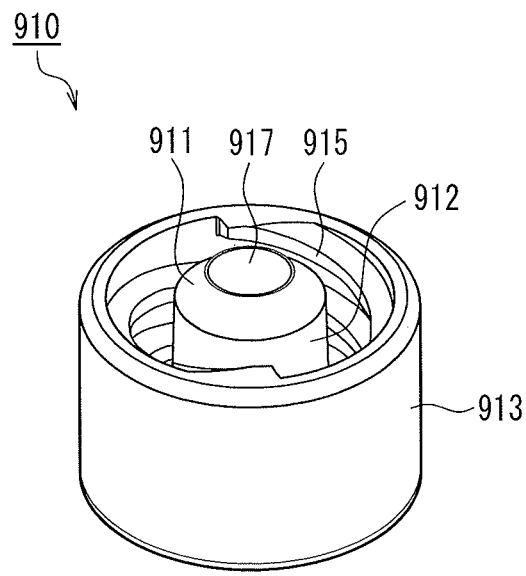
FIG. 11A is a perspective view of a male connector under consideration as ISO 80369-3.
Figure 11B:
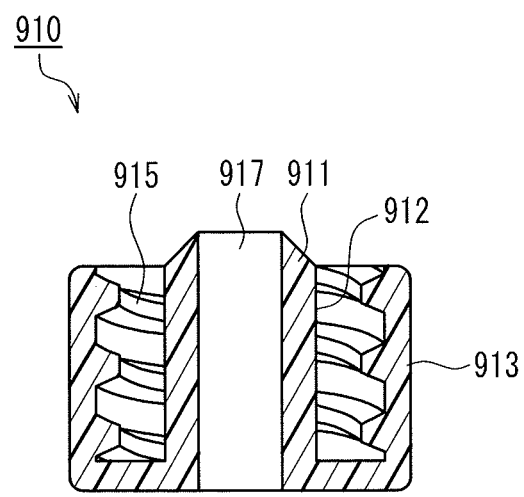
FIG. 11B is a cross-sectional view taken along a plane that includes the central axis of the male connector.
Figure 12A:
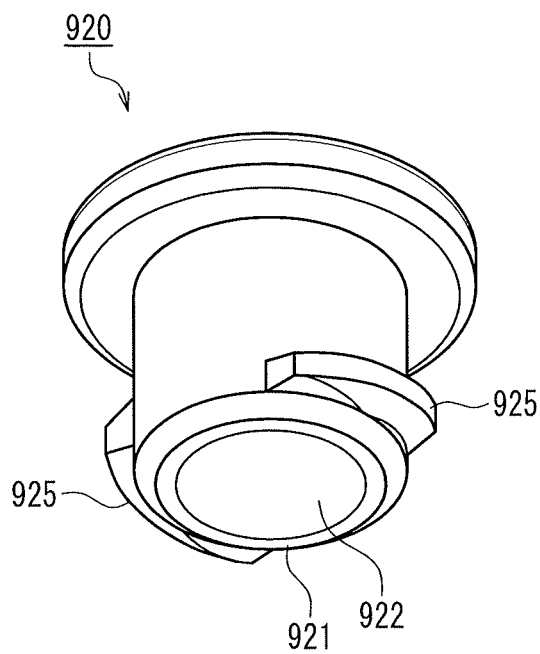
FIG. 12A is a perspective view of a female connector under consideration as ISO 80369-3.
Figure 12B:
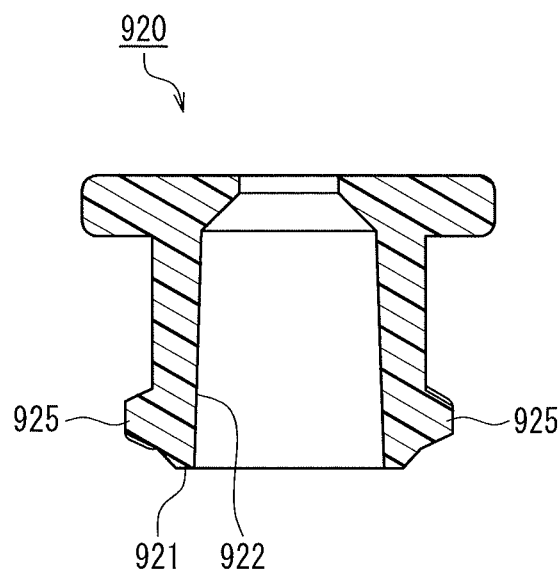
FIG. 12B is a cross-sectional view taken along a plane that includes the central axis of the female connector.

Thus, the lock portion 20 is attached to the luer portion 10, as shown in FIGS. 2A and 2B. FIG. 2A is a perspective view of the male connector 1 with the lock portion 20 attached to the luer portion 10, as viewed from above, and FIG. 2B is a cross-sectional view of the same taken along a plane that includes the central axis 1a. The spiral protrusion 14 and the second female threading 22 have been screwed together. The protruding portions 26 are fitted into the receding portions 16. The male luer 11 and the first female threading 21 that surrounds the male luer 11 are compliant with the above-described male connector 910 of ISO 80369-3 (FIGS. 11A and 11B). Accordingly, the male connector 1 can be connected to the female connector 920 compliant with ISO 80369-3 (FIGS. 12A and 12B).

The luer portion 10 and lock portion 20 can be separated by rotating the lock portion 20 relative to the luer portion 10, in the direction opposite to that during attachment. In order to begin rotation, the protruding portions 26 and the receding portions 16 need to be disengaged, and a somewhat large amount of rotation torque needs to be applied for disengagement. After the protruding portions 26 have escaped the receding portions 16, the lock portion 20 can be easily rotated relative to the luer portion 10 with a small rotation torque. Thus, the luer portion 10 and the lock portion 20 can be separated as shown in FIGS. 1A to 1D.

When the lock portion 20 is to be attached to or detached from the luer portion 10, the luer portion 10 can be grasped easily by pinching the pair of protrusions 19 with one's fingers, and rotation torque can be applied easily.

The attachment and detachment of the luer portion 10 and the lock portion 20 can be repeatedly performed any number of times.

Method of Use

The following describes a method of using the male connector 1 in the case where the male connector 1 is attached to the upstream end of a PEG catheter. In this case, the tube 8 is a PEG catheter, and the lower end thereof (not shown) is inserted into the patient's stomach. The male connector 1 is, along with the tube 8 (PEG catheter), indwelled in the patient in a state in which the lock portion 20 is attached to the luer portion 10 (FIGS. 2A and 2B).

In the case of performing enteral feeding, the female connector connected to the downstream end of a tube (container-side tube) connected to the container storing an enteral nutrient is connected to the male connector 1. The female connector is the female connector 920 compliant with ISO 80369-3 (FIGS. 12A and 12B). The male connector 1 and the female connector 920 can be connected by inserting the male luer 11 into the insertion portion 921 and screwing the first female threading 21 and the male threading 925 together. At this time, rotation torque can be easily applied to the luer portion 10 by pinching the pair of protrusions 19 of the luer portion 10 with one's fingers. The protruding portions 26 of the lock portion 20 are fitted into the receding portions 16 of the luer portion 10, and the lower face 20a of the lock portion 20 is in contact with the upper face 15a of the flange 15 of the luer portion 10. Accordingly, when the luer portion 10 is rotated, the lock portion 20 rotates integrally with the luer portion 10.

The outer circumferential face 12 of the male luer 11 is a tapered face that has the same taper angle as the inner circumferential face 922 of the insertion portion 921. Accordingly, they come into liquid-tight surface contact with each other. The connection between the male connector 1 and the female connector 920 is excellent in terms of liquid-tightness and connection strength, similarly to the connection between the male connector 910 (FIGS. 11A and 11B) and the female connector 920. When the male connector 1 and the female connector 920 are in the connected state, an enteral nutrient is administered to the patient via the tube 8.

Thereafter, the male connector 1 and the female connector 920 are separated. Separation can be performed by rotating the female connector 920 relative to the male connector 1 in the direction opposite to that during attachment so as to unscrew the first female threading 21 and the male threading 925. At this time as well, rotation torque in the direction opposite to that during connection can be applied to the luer portion 10 by pinching the pair of protrusions 19 of the luer portion 10 with one's fingers. The protruding portions 26 of the lock portion 20 have been fitted into the receding portions 16 of the luer portion 10. Accordingly, when the female connector 920 is rotated relative to the luer portion 10, the screwing together of the first female threading 21 and the male threading 925 is selectively loosened, without loosening the screwing together of the spiral protrusion 14 and the second female threading 22.

There are cases where an enteral nutrient has become stuck on the male connector 1 after the female connector 920 has been separated. In this case, the lock portion 20 can be further separated from the luer portion 10 in order to clean the male connector 1. The detached lock portion 20 can be cleaned by washing with water or the like. While connected to the tube 8, an enteral nutrient can be wiped off the luer portion 10 using a clean cloth, or the luer portion 10 can be cleaned by being rinsed in water stored in a container, for example. After the luer portion 10 and the lock portion 20 have been cleaned separately, the lock portion 20 is attached to the luer portion 10. If the lock portion 20 is very dirty, the lock portion 20 can be replaced with a new one instead of being cleaned.

Effects

As described above, the male connector 1 of Embodiment 1 includes the male luer 11 and the first female threading 21 that surrounds the male luer 11. Accordingly, the male connector 1 can be connected to the female connector 920 that is compliant with ISO 80369-3 and includes the insertion portion 921 for receiving insertion of the male luer 11 and the male threading 925 that is to be screwed together with the first female threading 21.

The male connector 1 is made up of two parts, namely the luer portion 10 that includes the male luer 11, and the lock portion 20 that includes the first female threading 21. The lock portion 20 can be repeatedly attached to and detached from the luer portion 10. Accordingly, if the male connector 1 becomes dirty due to an enteral nutrient becoming stuck to it, it is possible to separate the luer portion 10 and the lock portion 20 and clean them separately. After the lock portion 20 is detached from the luer portion 10, the outer circumferential face 12 of the male luer 11 is exposed (see FIG. 1A), and therefore can be cleaned by being wiped even if the luer portion 10 is connected to the tube 8. The spiral protrusion 14 is a discontinuous thread, and therefore the vicinity of the spiral protrusion 14 can also be cleaned easily. Meanwhile, the lock portion 20 that was detached from the luer portion 10 can be easily washed with water or the like. The male luer 11 is not present inside the lock portion 20, and both ends of the lock portion 20 are open, thus making it possible for an enteral nutrient stuck to the valleys of the female threading 21 and 22 to be removed by insertion of a brush or the like. The lock portion 20 can therefore also be cleaned. If impurities are firmly stuck to the lock portion 20, it is also possible to replace only the lock portion 20 with a new one. Accordingly, the male connector 1 of Embodiment 1 includes the male luer 11 and the first female threading 21 that surrounds the male luer 11, and can be easily maintained in a sanitary state.

The spiral protrusion 14 of the luer portion 10 and the second female threading 22 of the lock portion 20 are screwed together. By being engaged (screwed) with each other, the spiral protrusion 14 and the second female threading 22 constitute separation prevention mechanisms for preventing the luer portion 10 and the lock portion 20 from becoming separated along the central axis 1a direction. The spiral protrusion 14 and the second female threading 22 that constitute the separation prevention mechanisms are engaged in the central axis 1a direction. When the spiral protrusion 14 and the second female threading 22 are screwed together, the connection strength between the luer portion 10 and the lock portion 20 in the central axis 1a direction is very large. Accordingly, the male connector 1 and the female connector 920 can be connected with liquid-tightness and a connection strength that are in compliance with ISO 80369-3. For example, when performing enteral feeding, enteral nutrients do not leak from the joining portion of the male connector 1 and the female connector 920, and the male connector 1 and the female connector 920 do not unintentionally become separated due to pressure applied to the enteral nutrient, tensile force acting on the tube 8, or the like.

Since the separation prevention mechanisms are constituted by screwing structures, the luer portion 10 and the lock portion 20 can be firmly connected, and moreover, the luer portion 10 and the lock portion 20 are easily connected/separated.

The pair of receding portions 16 of the luer portion 10 and the pair of protruding portions 26 of the lock portion 20 are fitted together. By engaging with each other (fitting together), the receding portions 16 and the protruding portions 26 constitute rotation prevention mechanisms for preventing the lock portion 20 from rotating relative to the luer portion 10. The receding portions 16 and the protruding portions 26 that constitute the rotation prevention mechanisms are engaged in the circumferential direction. It is possible to release the locked state of the rotation prevention mechanisms (i.e., the engaged state of the receding portions 16 and the protruding portions 26) and rotate the lock portion 20 relative to the luer portion 10, but a relatively large amount of force is necessary. For this reason, when the luer portion 10 and the female connector 920 are respectively gripped and rotated in mutually opposite directions in order to separate the male connector 1 and the female connector 920 that are connected to each other, the rotation prevention mechanisms cause the lock portion 20 to rotate integrally with the luer portion 10, and therefore the screwing together of the first female threading 21 and the male threading 925 is selectively loosened, without the screwing together of the spiral protrusion 14 and the second female threading 22 being loosened. Accordingly, the male connector 1 and the female connector 920 can be separated without the male connector 1 becoming disassembled. The amount of force (rotation torque) necessary for putting the rotation prevention mechanisms into the locked state and releasing the locked state can be adjusted by appropriately changing the dimensions, shape, and the like of the protruding portions 26 and the receding portions 16. For example, the aforementioned force (rotation torque) can be reduced by, for example, reducing the protruding height of the protruding portions 26 from the lower face 20a of the lock portion 20, rounding or chamfering the tips of the protruding portions 26, or chamfering the edges of the openings of the receding portions 16.

The rotation prevention mechanisms also are useful in firmly screwing the first female threading 21 and the male threading 925 together by respectively gripping the luer portion 10 and the female connector 920 when connecting the female connector 920 to the male connector 1.

Although the male connector 1 is constituted by two parts, namely the luer portion 10 and the lock portion 20, it includes the rotation prevention mechanisms, and therefore the operability of connection to and separation from the female connector 920 is equivalent to the operability when the male connector 910 constituted by one part is connected to and separated from the female connector 920.

Since the luer portion 10 is connected to the tube 8, it is relatively difficult for the luer portion 10 to be detached from the tube 8 and replaced. In contrast, the lock portion 20 is detachable from the luer portion 10, and therefore can be replaced relatively easily. It is possible to employ a configuration that takes into consideration this difference in ease of replacement between the luer portion 10 and the lock portion 20.

For example, the protruding portions 26, which are portions protruding from a member, have a high possibility of colliding with another member and becoming damaged. Also, as the fitting and disengaging of the protruding portions 26 and the receding portions 16 to and from each other is repeated, the tips of the protruding portions 26 tend to become worn. In view of this, in Embodiment 1, the protruding portions 26 that are relatively likely to become damaged and worn are formed on the lock portion 20, and the receding portions 16 that are relatively unlikely to become damaged and worn are formed on the luer portion 10. Accordingly, if the protruding portions 26 become damaged or worn, and the functionality of the rotation prevention mechanisms degrades, the lock portion 20 can be replaced with a new one. Also, due to the receding portions 16 that are subjected to relatively little damage and wearing being formed on the luer portion 10, the lifetime of the luer portion 10 is extended. This is advantageous to reducing the frequency of replacement of the tube 8 that is provided with the luer portion 10.

Also, the luer portion 10 can be constituted using a harder material than the lock portion 20. Accordingly, it is possible to reduce damage to and wearing of the luer portion 10. It is therefore possible to further extend the lifetime of the luer portion 10. This is advantageous to reducing the frequency of replacement of the tube 8 that is provided with the luer portion 10.

Embodiment 2

Configuration

A male connector 2 of Embodiment 2 does not include the spiral protrusion 14 and the second female threading 22 included in the male connector 1 of Embodiment 1. The male connector 2 of Embodiment 2 will be described with focus on differences from the male connector 1 of Embodiment 1. In the drawings referenced below, elements the same as or corresponding to elements of the male connector 1 of Embodiment 1 are denoted by the same reference signs, and detailed descriptions will not be given for them.

Figure 3A:
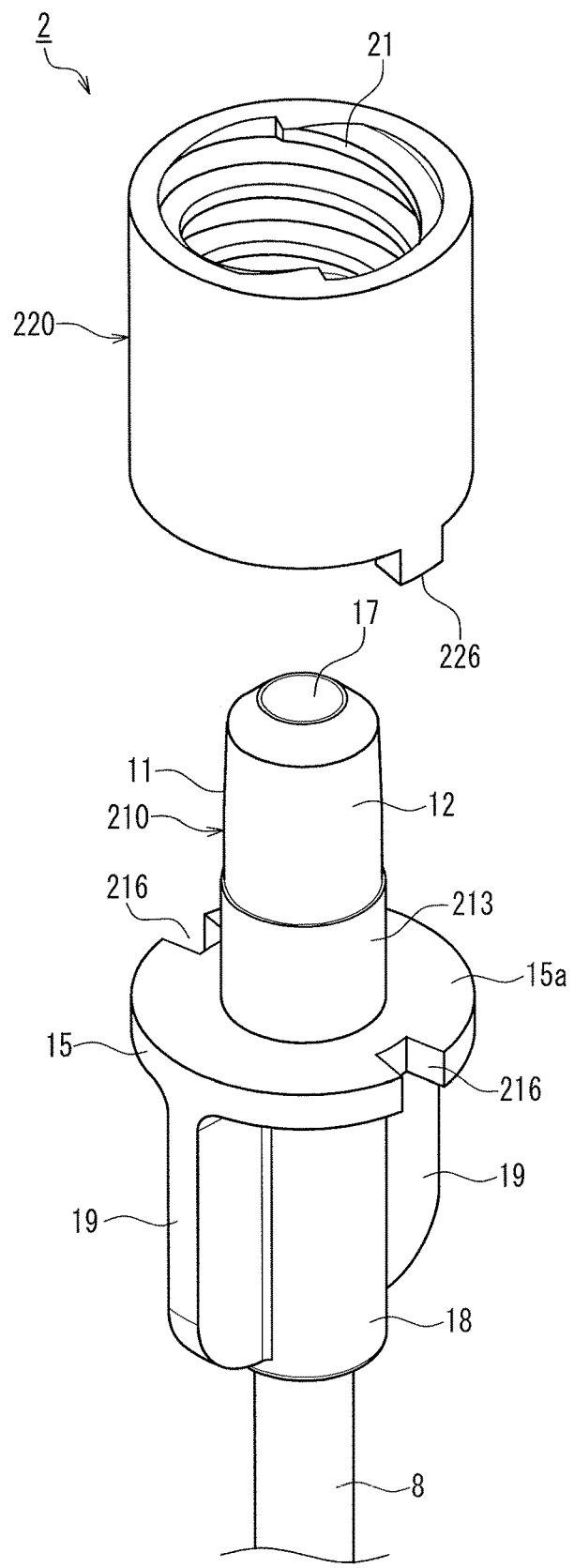
FIG. 3A is an exploded perspective view of a male connector according to Embodiment 2 of the present invention, as viewed from above.
Figure 3B:
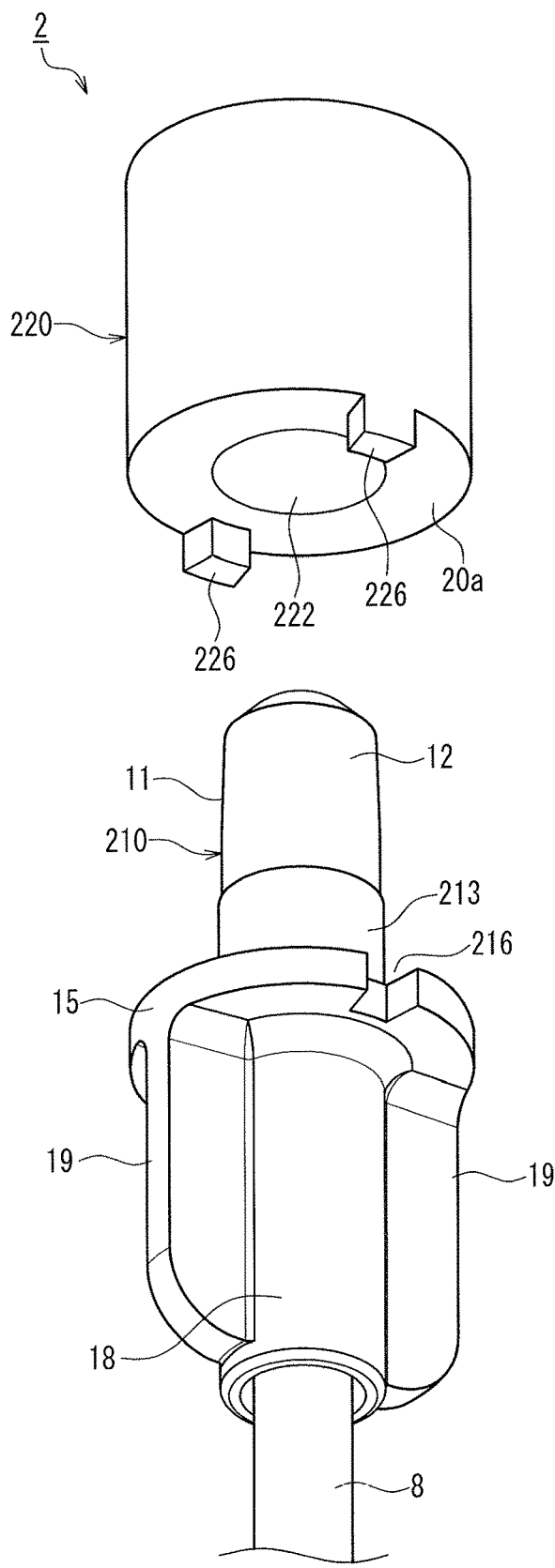
FIG. 3B is an exploded perspective view of the male connector according to Embodiment 2 of the present invention, as viewed from below.
Figure 3C:
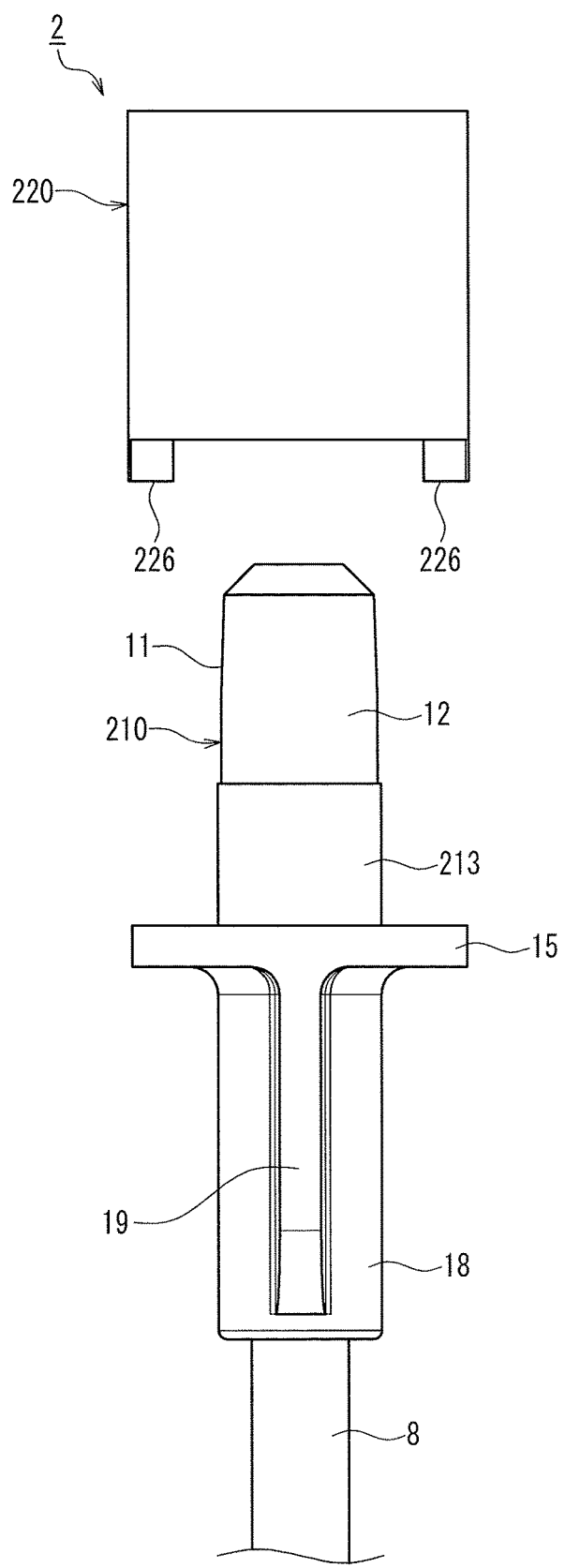
FIG. 3C is an exploded side view of the male connector according to Embodiment 2 of the present invention.
Figure 3D:
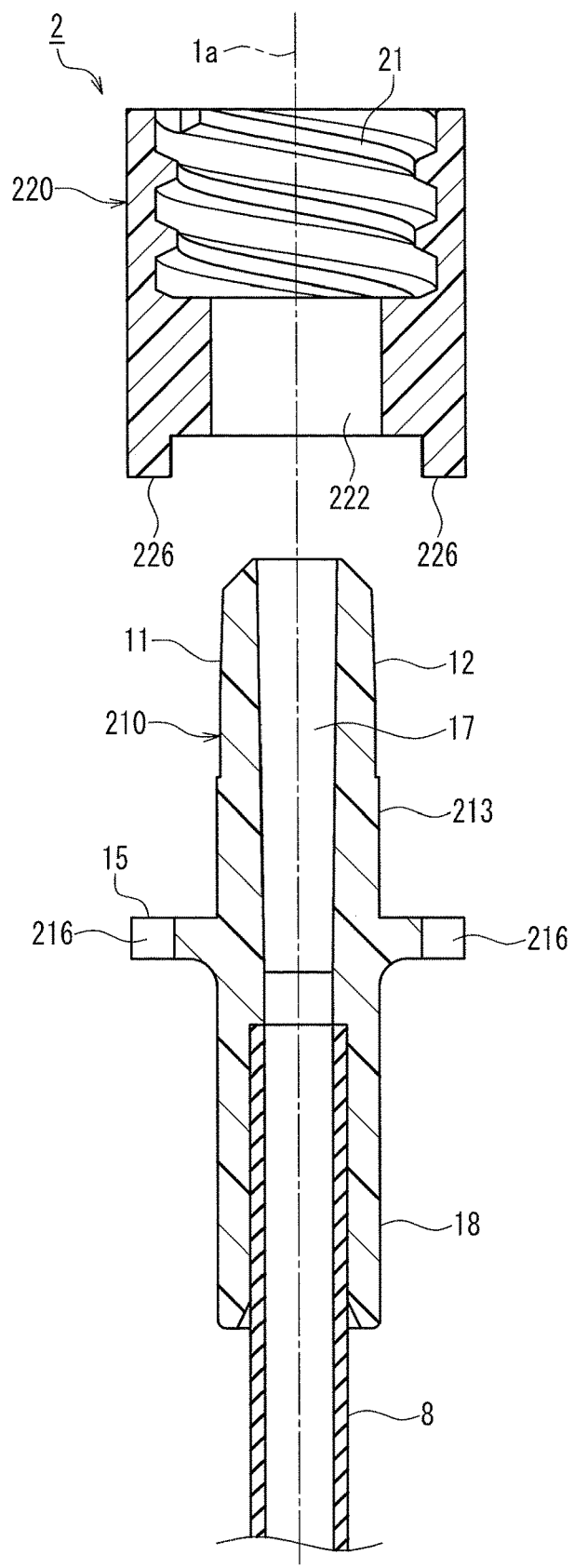
FIG. 3D is an exploded cross-sectional view taken along a plane that includes the central axis of the male connector according to Embodiment 2 of the present invention.

FIG. 3A is an exploded perspective view of the male connector 2 according to Embodiment 2 of the present invention, as viewed from above. FIG. 3B is an exploded perspective view of the male connector 2, as viewed from below. FIG. 3C is an exploded side view of the male connector 2. FIG. 3D is an exploded cross-sectional view taken along a plane that includes the central axis 1a of the male connector 2.

Similarly to the male connector 1 of Embodiment 1, the male connector 2 of Embodiment 2 includes a luer portion 210 and a lock portion 220.

As shown in FIGS. 3A and 3B, the luer portion 210 is provided with a tubular portion 213 between the male luer 11 and the flange 15. The outer circumferential face of the tubular portion 213 is a cylindrical face whose outer diameter is approximately constant in the central axis 1a direction. The spiral protrusion 14 provided on the tubular portion 13 of Embodiment 1 is not provided on the outer circumferential face of the tubular portion 213.

A pair of receding portions 216 are formed in the disc-shaped flange 15. The receding portions 216 are notches that pass through the flange 15 in the thickness direction. The pair of receding portions 216 are in rotation symmetry (two-fold symmetry) about the central axis 1a.

As shown in FIG. 3D, female threading 21 that corresponds to the first female threading 21 of Embodiment 1 is formed in the inner circumferential face of the lock portion 220. A cylindrical face 222 whose inner diameter is constant in the central axis 1a direction is formed below the female threading 21.

As shown in FIG. 3B, a pair of protruding portions 226 protrude downward from the lower face 20a of the lock portion 220. The protruding height of the protruding portions 226 from the lower face 20a is larger than that of the protruding portions 26 of Embodiment 1.

In Embodiment 2 as well, the lock portion 220 can be repeatedly attached to and detached from the luer portion 210. The attachment of the lock portion 220 to the luer portion 210 is performed as described below.

In Embodiment 2, the spiral protrusion 14 and the second female threading 22 included in the male connector 1 of Embodiment 1 are not provided. Accordingly, as shown in FIGS. 3A to 3D, the luer portion 210 and the lock portion 220 are arranged so as to oppose each other, and the male luer 11 is pressed into the lock portion 220. The tubular portion 213 of the luer portion 210 is fitted into the cylindrical face 222 of the lock portion 220, and the pair of protruding portions 226 of the lock portion 220 are fitted into the pair of receding portions 216 of the luer portion 210.

Figure 4A:
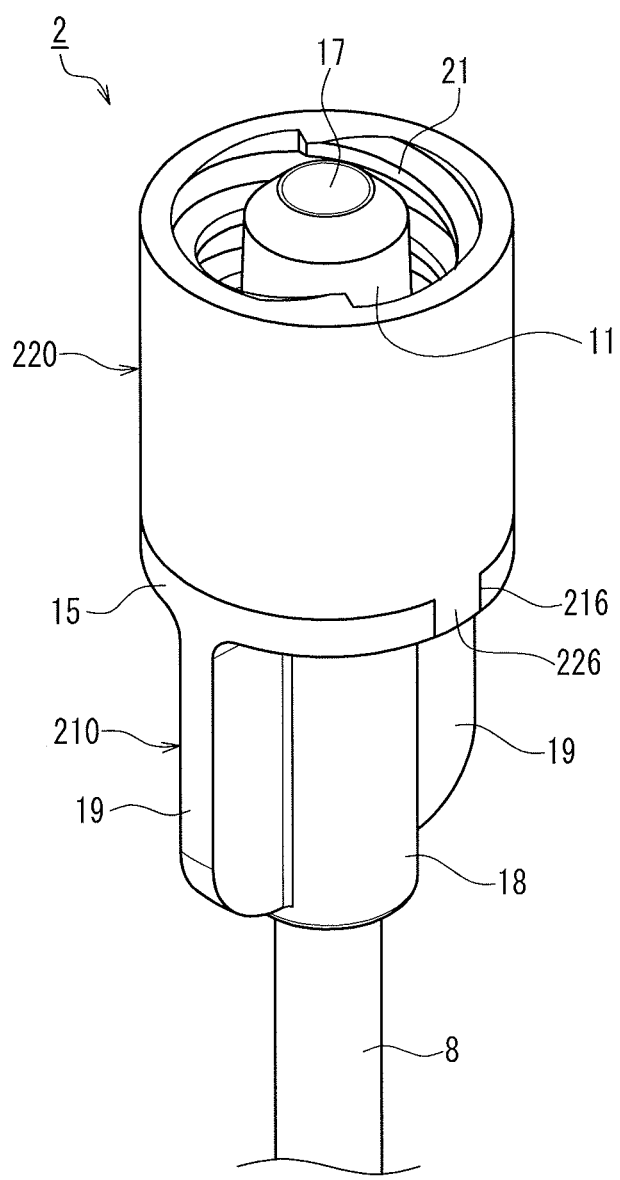
FIG. 4A is a perspective view of the male connector according to Embodiment 2 of the present invention, as viewed from above.
Figure 4B:
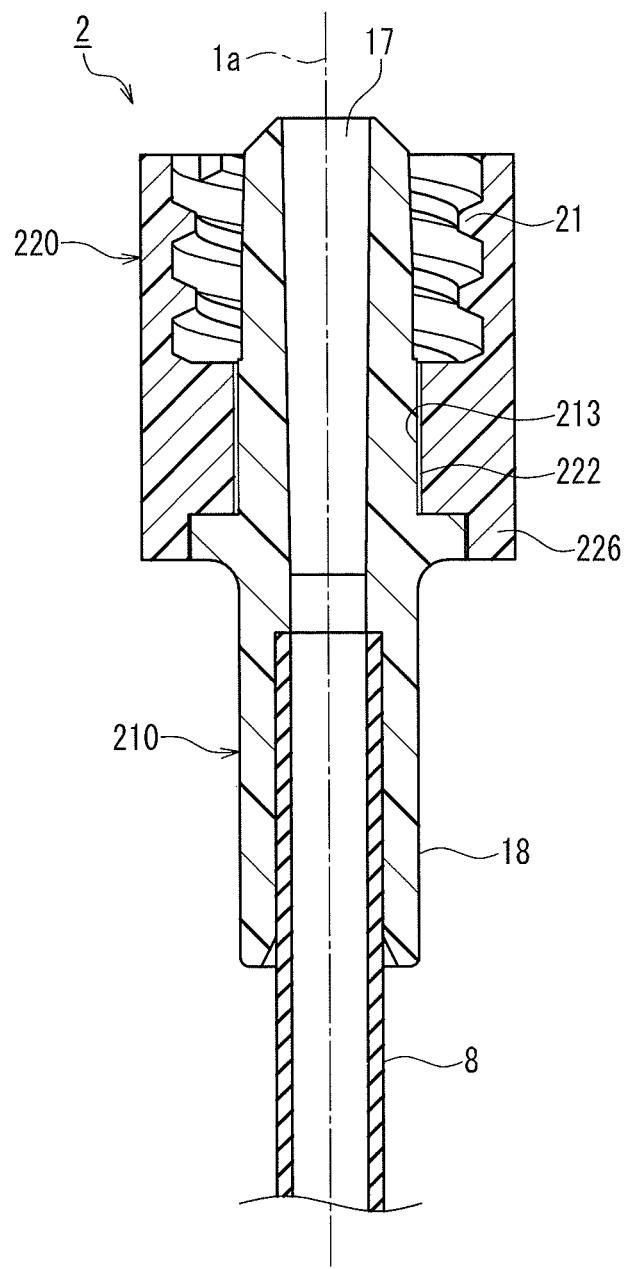
FIG. 4B is a cross-sectional view taken along a plane that includes the central axis of the male connector according to Embodiment 2 of the present invention.

Thus, the lock portion 220 is attached to the luer portion 210, as shown in FIGS. 4A and 4B. FIG. 4A is a perspective view of the male connector 2 with the lock portion 220 attached to the luer portion 210, as viewed from above, and FIG. 4B is a cross-sectional view of the same taken along a plane that includes the central axis 1a. The protruding portions 226 are fitted into the receding portions 216. The male luer 11 and the female threading 21 that surrounds the male luer 11 are compliant with the above-described male connector 910 of ISO 80369-3 (FIGS. 11A and 11B). Accordingly, similarly to Embodiment 1, the male connector 2 can be connected to the female connector 920 compliant with ISO 80369-3 (FIGS. 12A and 12B).

The luer portion 210 and the lock portion 220 can be separated by pulling the luer portion 210 and lock portion 220 in mutually opposite directions so as to separate along the central axis 1a direction. The fitting of the tubular portion 213 and the cylindrical face 222 and the fitting of the protruding portions 226 and the receding portions 216 are each released, and the luer portion 210 and the lock portion 220 can be separated as shown in FIGS. 3A to 3D.

The attachment and detachment of the luer portion 210 and the lock portion 220 can be repeatedly performed any number of times.

Method of Use

The method of use of the male connector 2 is approximately the same as the method of use of the male connector 1 of Embodiment 1. Similarly to Embodiment 1, the female connector 920 compliant with ISO 80369-3 (FIGS. 12A and 12B) can be connected to and separated from the male connector 2. The connection between the male connector 2 and the female connector 920 is excellent in terms of liquid-tightness and connection strength, similarly to the connection between the male connector 910 (FIGS. 11A and 11B) and the female connector 920.

After performing enteral feeding, similarly to Embodiment 1, the lock portion 220 can be separated from the luer portion 210, and they can be cleaned separately. The lock portion 220 may be replaced with a new one instead of being cleaned.

Effects

Similarly to the male connector 1 of Embodiment 1, the male connector 2 of Embodiment 2 can be connected to the female connector 920 that is compliant with ISO 80369-3 and includes the insertion portion 921 for receiving insertion of the male luer 11 and the male threading 925 that is to be screwed together with the female threading 21.

The male connector 2 is made up of two parts, namely the luer portion 210 that includes the male luer 11 and the lock portion 220 that includes the female threading 21, and the lock portion 220 can be repeatedly attached to and detached from the luer portion 210. Accordingly, similarly to Embodiment 1, the luer portion 210 and the lock portion 220 can be separated, and they can be cleaned separately. If impurities are firmly stuck to the lock portion 220, it is also possible to replace only the lock portion 220 with a new one. Accordingly, the male connector 2 of Embodiment 2 includes the male luer 11 and the female threading 21 that surrounds the male luer 11, and can be easily maintained in a sanitary state.

The spiral protrusion 14 of Embodiment 1 is not provided on the tubular portion 213 of the luer portion 210. Accordingly, the tubular portion 213 can be cleaned easily. Also, the second female threading 22 of Embodiment 1 is not provided in the inner circumferential face of the lock portion 220. Accordingly, the inner circumferential face of the lock portion 220 can be cleaned easily.

The male connector 2 of Embodiment 2 does not include the spiral protrusion 14 and the second female threading 22 that are provided in the male connector 1 of Embodiment 1 and constitute separation prevention mechanisms. Accordingly, if the pressure of the enteral nutrient flowing through the tube 8 rises, or tensile force is applied to the tube 8 while the female connector 920 is connected to the male connector 2, it is possible for the luer portion 210 and the lock portion 220 to become separated. However, the connection strength between the luer portion 210 and the lock portion 220 can be adjusted by appropriately designing the fitting of the protruding portions 226 and the receding portions 216 and/or the fitting of the tubular portion 213 and the cylindrical face 222. Accordingly, in Embodiment 2 as well, the male connector 2 and the female connector 920 can be connected with liquid-tightness and a connection strength that are in compliance with ISO 80369-3.

In Embodiment 2, the connection strength between the luer portion 210 and the lock portion 220 can be set such that the luer portion 210 and the lock portion 220 become separated if the internal pressure in the tube 8 rises abnormally, or if an abnormally large amount of tensile force is applied to the tube 8. There are cases where this is preferable from the viewpoint of ensuring the safety of the patient and a caregiver.

By engaging with each other (fitting together), the receding portions 216 and the protruding portions 226 constitute rotation prevention mechanisms for preventing the lock portion 220 from rotating relative to the luer portion 210. The receding portions 216 and the protruding portions 226 that constitute the rotation prevention mechanisms are engaged in the circumferential direction. The rotation prevention mechanisms make it possible for the female connector 920 to be connected to and separated from the male connector 2 by respectively gripping the luer portion 210 and the female connector 920 and rotating them in mutually opposite directions.

In Embodiment 1, the lock portion 20 needs to be rotated relative to the luer portion 10 when connecting/separating the luer portion 10 and the lock portion 20. Accordingly, the protruding portions 26 and receding portions 16 that constitute the rotation prevention mechanisms need to be configured such that the protruding portions 26 and the receding portions 16 can be engaged (fitted together) and disengaged in the case where the lock portion 20 is rotated relative to the luer portion 10 with a relatively large amount of rotation torque. In contrast, in Embodiment 2, there is no need to rotate the lock portion 220 relative to the luer portion 210 when connecting/separating the luer portion 210 and the lock portion 220. Accordingly, the protruding portions 226 and the receding portions 216 that constitute the rotation prevention mechanisms of Embodiment 2 can be designed so as to more forcefully prevent rotation of the lock portion 220 relative to the luer portion 210. Accordingly, it is possible to respectively grip the luer portion 210 and the female connector 920 and connect the male connector 2 and the female connector 920 more firmly, or separate the firmly-connected male connector 2 and female connector 920.

Embodiment 2 is the same as Embodiment 1 with the exception of the content described above. The description of Embodiment 1 applies to Embodiment 2 as well.

Embodiment 3

Configuration

A male connector 3 of Embodiment 3 has mainly the following two differences from the male connector 1 of Embodiment 1. Firstly, a lock portion 320 has a pair of extension portions 325 that extend downward. Secondly, a liquid-tight seal is formed between a luer portion 310 and the lock portion 320. The male connector 3 of Embodiment 3 will be described with focus on differences from the male connector 1 of Embodiment 1. In the drawings referenced below, elements the same as or corresponding to elements of the male connector 1 of Embodiment 1 are denoted by the same reference signs, and detailed descriptions will not be given for them.

Figure 5A:
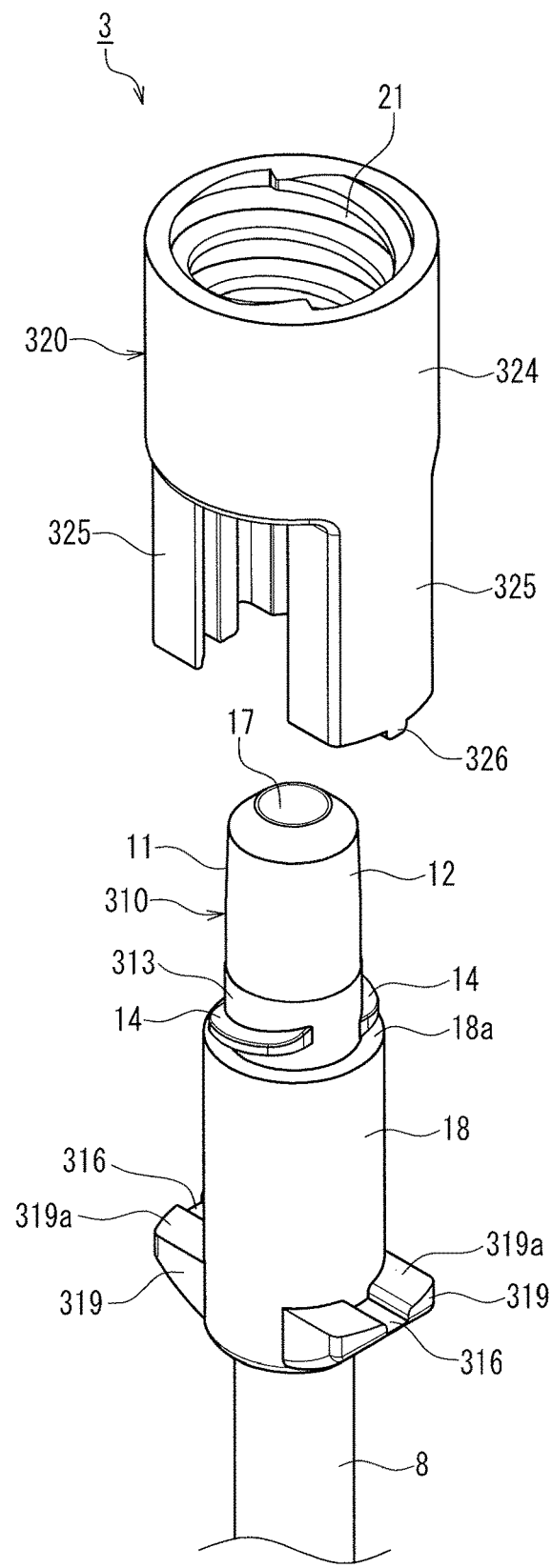
FIG. 5A is an exploded perspective view of a male connector according to Embodiment 3 of the present invention, as viewed from above.
Figure 5B:
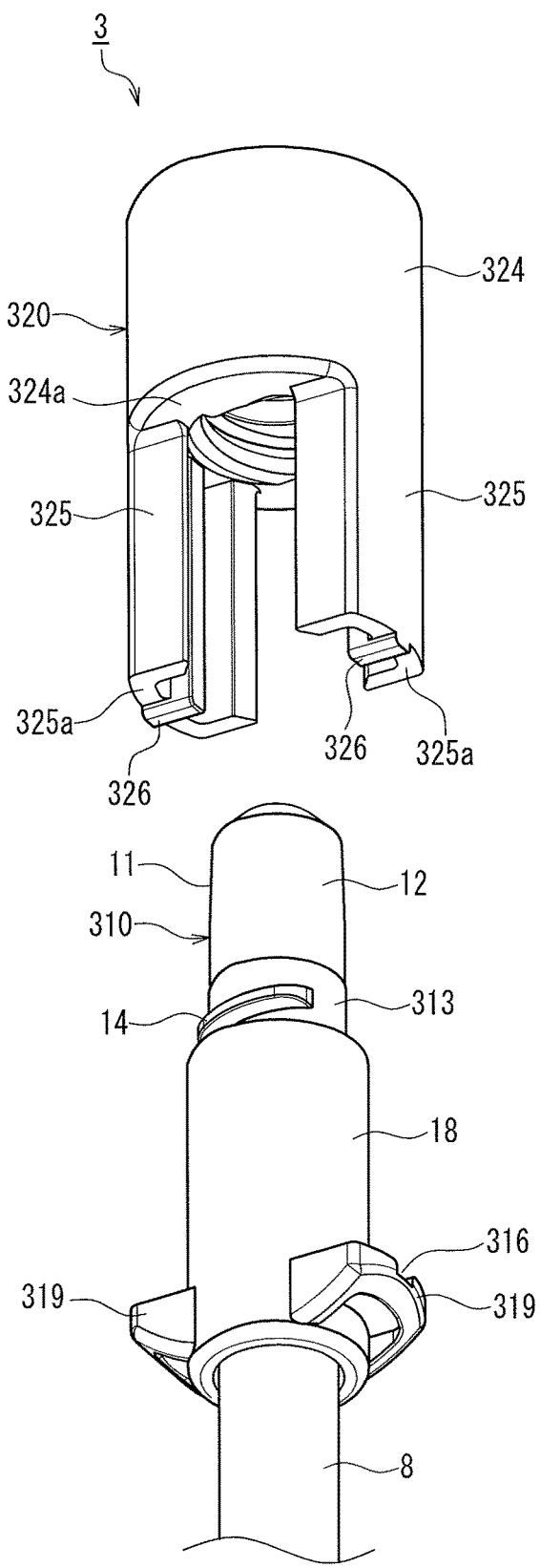
FIG. 5B is an exploded perspective view of the male connector according to Embodiment 3 of the present invention, as viewed from below.
Figure 5C:
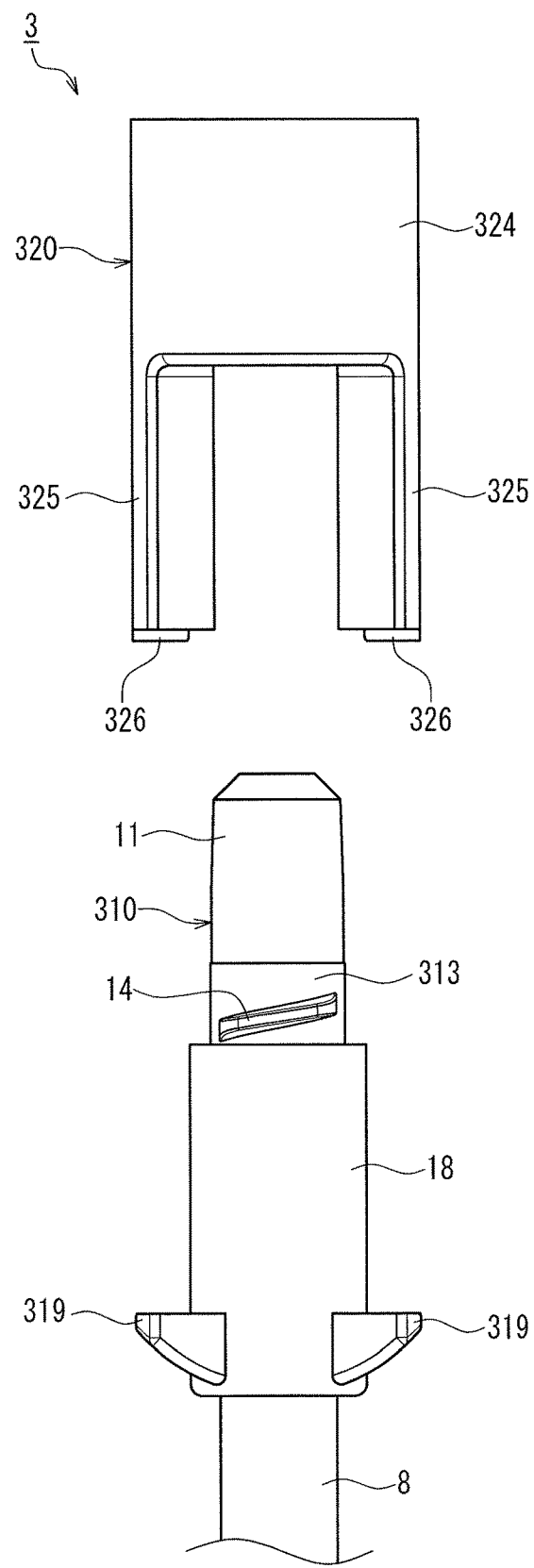
FIG. 5C is an exploded side view of the male connector according to Embodiment 3 of the present invention.
Figure 5D:
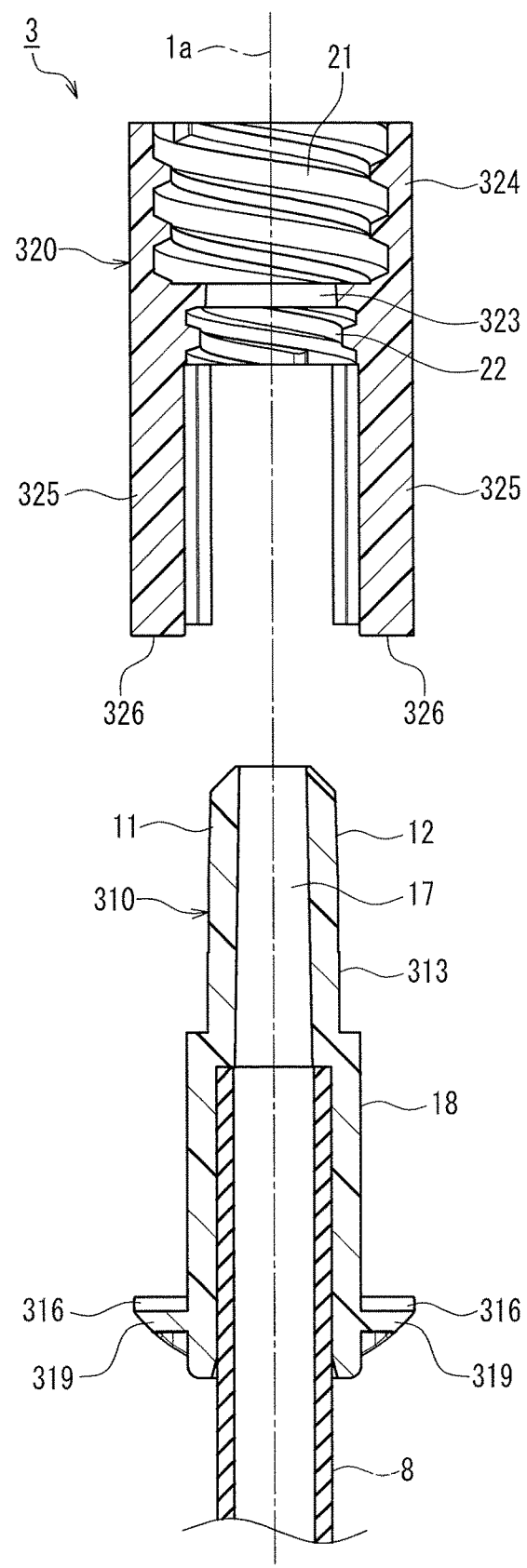
FIG. 5D is an exploded cross-sectional view taken along a plane that includes the central axis of the male connector according to Embodiment 3 of the present invention.

FIG. 5A is an exploded perspective view of the male connector 3 according to Embodiment 3 of the present invention, as viewed from above. FIG. 5B is an exploded perspective view of the male connector 3, as viewed from below. FIG. 5C is an exploded side view of the male connector 3. FIG. 5D is an exploded cross-sectional view taken along a plane that includes the central axis 1a of the male connector 3.

Similarly to the male connector 1 of Embodiment 1, the male connector 3 of Embodiment 3 includes the luer portion 310 and the lock portion 320.

As shown in FIGS. 5A and 5B, the luer portion 310 does not include the flange 15 (see FIGS. 1A and 1B) included in the luer portion 10 of Embodiment 1. The male luer 11 is provided upright on an upper face 18a of the base end portion 18. The outer circumferential face of the base end portion 18 is a cylindrical face that is coaxial with the male luer 11. The outer diameter of the base end portion 18 is the same as or larger than the maximum diameter of the spiral protrusion 14.

A pair of protrusions 319 protrude outward along the radial direction at positions in the vicinity of the lower end of the outer circumferential face of the base end portion 18. Unlike the protrusions 19 of Embodiment 1, the protrusions 319 are shaped as thin plates that extend in the circumferential direction. Upper faces 319a of the protrusions 319 are flat surfaces that are perpendicular to the central axis 1a. Receding portions 316 are formed in the upper faces 319a of the protrusions 319. The pair of protrusions 319 and the pair of receding portions 316 are in rotation symmetry (two-fold symmetry) about the central axis 1a.

A tubular portion 313 is provided between the male luer 11 and the base end portion 18. Unlike the tubular portion 13 of Embodiment 1, the outer circumferential face of the tubular portion 313 is a tapered face whose outer diameter decreases as it approaches the male luer 11 (a so-called male tapered face). A spiral protrusion 14 similar to that of Embodiment 1 protrudes from the outer circumferential face of the tubular portion 313.

The lock portion 320 includes a lock portion body 324 that has a hollow, approximately cylindrical shape, and is open at the two ends in the up-down direction. A pair of extension portions 325 extend downward from a lower face 324a of the lock portion body 324. The extension portions 325 are bar-shaped (arm-shaped) members that extend in the up-down direction. The gap between the pair of extension portions 325 is the same as or slightly larger than the outer diameter of the base end portion 18 of the luer portion 310. The outer dimension at the pair of extension portions 325 is approximately the same as the outer dimension at the pair of protrusions 319 of the luer portion 310. Lower faces 325a of the extension portions 325 are flat surfaces that are perpendicular to the central axis 1a. Protruding portions 326 protrude downward from the lower faces 325a of the extension portions 325. The pair of extension portions 325 and the pair of protruding portions 326 are in rotation symmetry (two-fold symmetry) about the central axis 1a.

As shown in FIG. 5D, similarly to the lock portion 20 of Embodiment 1, in order from the top, first female threading 21 and second female threading 22 are formed in the inner circumferential face of the lock portion body 324. A small diameter portion 323 is provided between the first female threading 21 and the second female threading 22. The inner circumferential face of the small diameter portion 323 is a tapered face whose inner diameter increases as it approaches the second female threading 22 (a so-called female tapered face). The minimum inner diameter of the small diameter portion 323 is smaller than the minimum inner diameter of the first female threading 21 and the minimum inner diameter of the second female threading 22. The female tapered face of the small diameter portion 323 has the same taper angle and diameter as the male tapered face of the tubular portion 313 of the luer portion 310.

In Embodiment 3 as well, the lock portion 320 can be repeatedly attached to and detached from the luer portion 310. The attachment of the lock portion 320 to the luer portion 310 is approximately the same as in Embodiment 1, and is performed as described below.

As shown in FIGS. 5A to 5D, the luer portion 310 and the lock portion 320 are arranged so as to oppose each other. The male luer 11 is inserted into the lock portion 320 from the lower side thereof. The male luer 11 and the base end portion 18 are inserted between the pair of extension portions 325 in the stated order. The spiral protrusion 14 of the luer portion 310 collides with the thread ridge of the second female threading 22 of the lock portion 320. The lock portion 320 is rotated relative to the luer portion 310, thus screwing the spiral protrusion 14 and the second female threading 22 together. As the lock portion 20 is rotated, the male luer 11 and the tubular portion 313 advance inside the lock portion body 324 in the stated order. The protruding portions 326 of the extension portions 325 soon come into contact with the upper faces 319a of the protrusions 319 of the luer portion 310, and slide thereon. Finally, the protruding portions 326 are fitted into the receding portions 316 of the luer portion 310, and, at the same time, the lower faces 325a of the extension portions 325 and the upper faces 319a of the protrusions 319 oppose each other. When the pair of protruding portions 326 are fitted into the pair of receding portions 316, the rotation torque for rotating the lock portion 320 changes, and the operator can feel that change as a clicking sensation through their fingers.

Figure 6A:
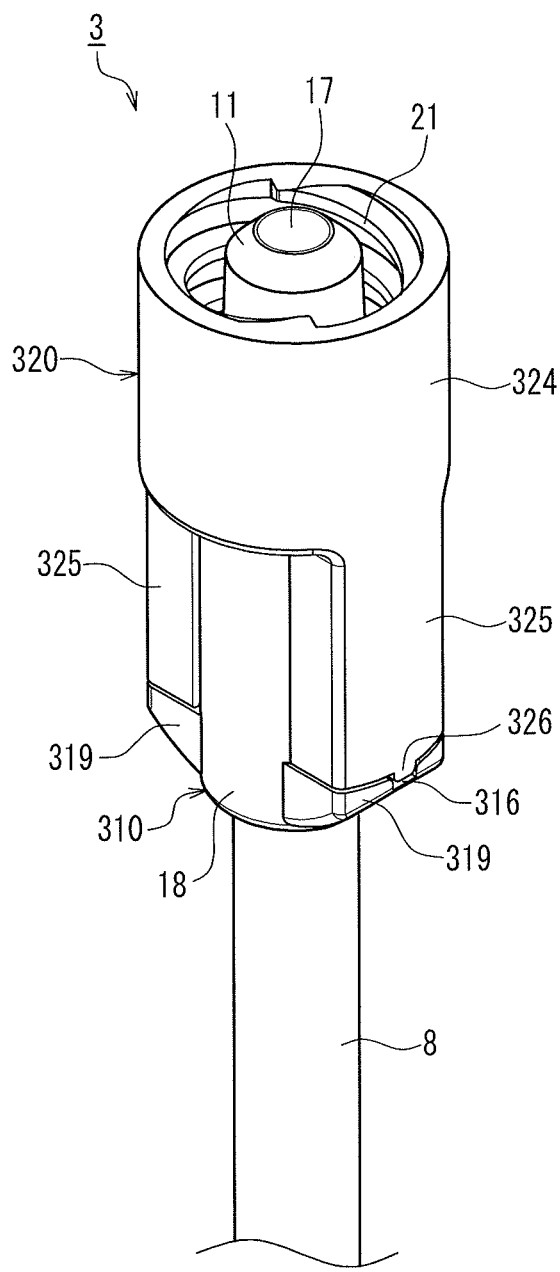
FIG. 6A is a perspective view of the male connector according to Embodiment 3 of the present invention, as viewed from above.
Figure 6B:
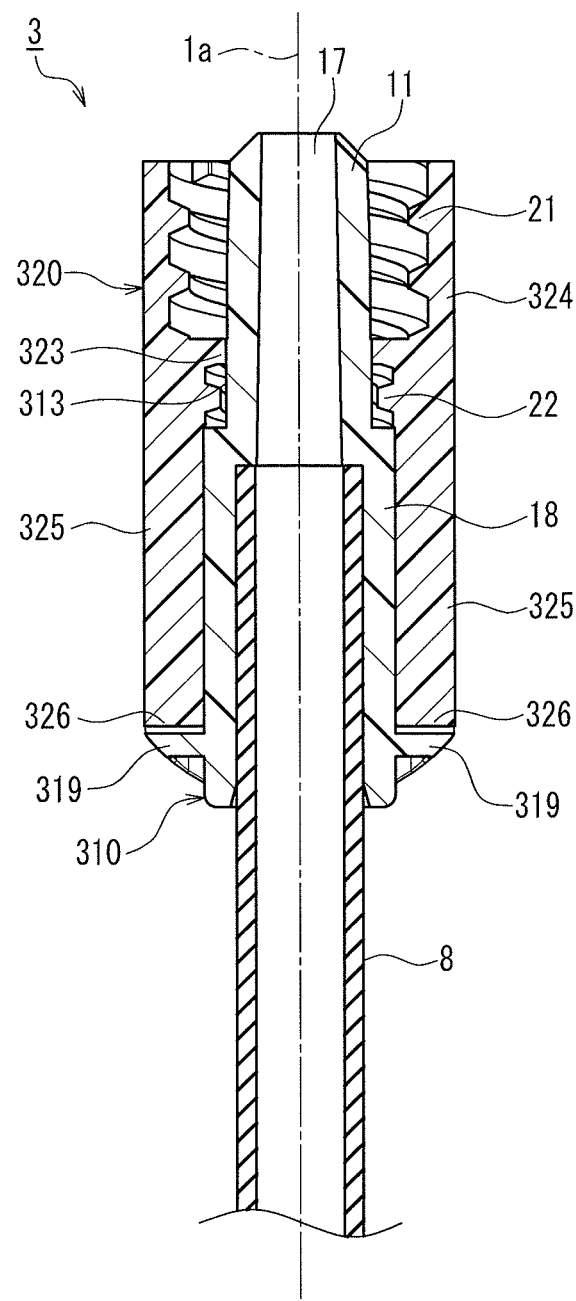
FIG. 6B is a cross-sectional view taken along a plane that includes the central axis of the male connector according to Embodiment 3 of the present invention.
Figure 6C:
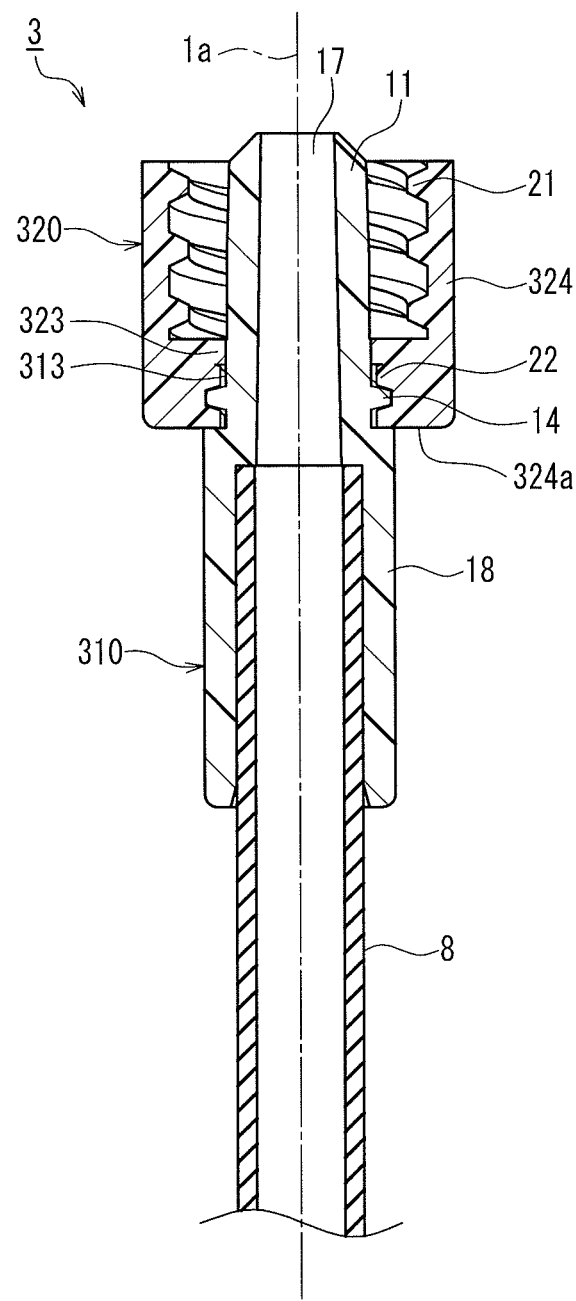
FIG. 6C is a cross-sectional view taken along a different plane that includes the central axis of the male connector according to Embodiment 3 of the present invention.

Thus, the lock portion 320 is attached to the luer portion 310, as shown in FIGS. 6A to 6C. FIG. 6A is a perspective view of the male connector 3 with the lock portion 320 attached to the luer portion 310, as viewed from above. FIG. 6B is a cross-sectional view of the male connector 3 taken along a plane that includes the central axis 1a and the extension portions 325. FIG. 6C is a cross-sectional view of the male connector 3 taken along a different plane that includes the central axis 1a. The cross-section in FIG. 6C is orthogonal to the cross-section in FIG. 6B.

As shown in FIG. 6A, the pair of extension portions 325 of the lock portion 320 oppose the base end portion 18 of the luer portion 310 in the radial direction, and are arranged on respective sides of the base end portion 18. The extension portions 325 and the protrusions 319 oppose each other in the up-down direction, and the exposed outer faces of the extension portions 325 constitute faces that are approximately continuous with the outer faces of the protrusions 319. The protruding portions 326 are fitted into the receding portions 316.

As shown in FIG. 6C, the spiral protrusion 14 and the second female threading 22 are screwed together. As shown in FIGS. 6B and 6C, the tubular portion 313 and the small diameter portion 323 are in surface contact with and fitted to each other.

The male luer 11 and the first female threading 21 that surrounds the male luer 11 are compliant with the above-described male connector 910 of ISO 80369-3 (FIGS. 11A and 11B). Accordingly, the male connector 3 can be connected to the female connector 920 compliant with ISO 80369-3 (FIGS. 12A and 12B).

Similarly to Embodiment 1, the luer portion 310 and lock portion 320 can be separated by rotating the lock portion 320 relative to the luer portion 310, in the direction opposite to that during attachment. In order to begin rotation, the protruding portions 326 and the receding portions 316 need to be disengaged, and a somewhat large amount of rotation torque needs to be applied for disengagement. After the protruding portions 326 have escaped the receding portions 316, the lock portion 320 can be easily rotated relative to the luer portion 310 with a small rotation torque. Thus, the luer portion 310 and the lock portion 320 can be separated as shown in FIGS. 5A to 5D.

When the lock portion 320 is to be attached to or detached from the luer portion 310, the pair of protrusions 319 are pinched with one hand, and the lock portion body 324 is pinched with the other hand.

The attachment and detachment of the luer portion 310 and the lock portion 320 can be repeatedly performed any number of times.

Method of Use

The method of use of the male connector 3 is approximately the same as the method of use of the male connector 1 of Embodiment 1. Similarly to Embodiment 1, the female connector 920 compliant with ISO 80369-3 (FIGS. 12A and 12B) can be connected to and separated from the male connector 3. The connection between the male connector 3 and the female connector 920 is excellent in terms of liquid-tightness and connection strength, similarly to the connection between the male connector 910 (FIGS. 11A and 11B) and the female connector 920.

After performing enteral feeding, similarly to Embodiment 1, the lock portion 320 can be separated from the luer portion 310, and they can be cleaned separately. The lock portion 320 may be replaced with a new one instead of being cleaned.

Effects

Similarly to the male connector 1 of Embodiment 1, the male connector 3 of Embodiment 3 can be connected to the female connector 920 that is compliant with ISO 80369-3 and includes the insertion portion 921 for receiving insertion of the male luer 11 and the male threading 925 that is to be screwed together with the first female threading 21.

The male connector 3 is made up of two parts, namely the luer portion 310 that includes the male luer 11 and the lock portion 320 that includes the first female threading 21, and the lock portion 320 can be repeatedly attached to and detached from the luer portion 310. Accordingly, similarly to Embodiment 1, the luer portion 310 and the lock portion 320 can be separated, and they can be cleaned separately. If impurities are firmly stuck to the lock portion 320, it is also possible to replace only the lock portion 320 with a new one. Accordingly, the male connector 3 of Embodiment 3 includes the male luer 11 and the first female threading 21 that surrounds the male luer 11, and can be easily maintained in a sanitary state.

Similarly to Embodiment 1, by being engaged (screwed) with each other, the spiral protrusion 14 of the luer portion 310 and the second female threading 22 of the lock portion 320 constitute separation prevention mechanisms for preventing the luer portion 310 and the lock portion 320 from becoming separated along the central axis 1a direction. Accordingly, the male connector 3 and the female connector 920 can be connected with liquid-tightness and a connection strength that are in compliance with ISO 80369-3. Since the separation prevention mechanisms are constituted by screwing structures, the luer portion 310 and the lock portion 320 can be firmly connected, and moreover, the luer portion 310 and the lock portion 320 are easily connected/separated.

Similarly to Embodiment 1, by engaging with each other (fitting together), the pair of receding portions 316 of the luer portion 310 and the pair of protruding portions 326 of the lock portion 320 constitute rotation prevention mechanisms for preventing the lock portion 320 from rotating relative to the luer portion 310. The rotation prevention mechanisms prevent the screwing together of the spiral protrusion 14 and the second female threading 22 from becoming loosened unintentionally.

In Embodiment 3, as shown in FIG. 6A, when the lock portion 320 has been attached to the luer portion 310, the pair of extension portions 325 of the lock portion 320 are arranged radially outward relative to the base end portion 18 of the luer portion 310. The extension portions 325 protrude outward from the outer circumferential face of the base end portion 18. The extension portions 325 reach the vicinity of the lower end of the base end portion 18. The vertical dimension from the lower ends of the extension portions 325 to the lower end of the base end portion 18 is preferably greater than or equal to half of the vertical dimension of the base end portion 18, more preferably greater than or equal to ⅔ of the same, and particularly preferably greater than or equal to ¾ of the same. Also, the vertical dimension of the extension portions 325 is much larger than the vertical dimension of the protrusions 319. Accordingly, if the base end portion 18 of the male connector 3 is gripped, the pair of extension portions 325 can also be gripped at the same time.

Similarly to Embodiment 1, the first female threading 21 and the male threading 925 need to be screwed together when connecting the male connector 3 and the female connector 920 (see FIGS. 12A and 12B), and the screwing together of the first female threading 21 and the male threading 925 needs to be loosened when separating the male connector 3 and the female connector 920. In such cases, the rotation torque for rotating the male connector 3 relative to the female connector 920 can be applied to the pair of extension portions 325 in Embodiment 3, rather than the pair of protrusions 319. The pair of extension portions 325 and the first female threading 21 are provided on the lock portion 320 in common. Accordingly, the rotation torque that is applied to the pair of extension portions 325 is reliably transmitted to the first female threading 21.

For example, if the male connector 3 and the female connector 920 (see FIGS. 12A and 12B) are left in the connected state for a long period of time, there are cases where a nutrient becomes stuck thereto, and it is difficult to loosen the screwing together of the first female threading 21 and the male threading 925. Also, if the male connector 3 and the female connector 920 are firmly twisted during connection, there are cases where it is difficult to thereafter loosen the screwing together of the first female threading 21 and the male threading 925. In such a case as well, the screwing together of the first female threading 21 and the male threading 925 can be loosened by applying a large amount of rotation torque to the pair of extension portions 325.

In contrast, with the connector 1 (see FIG. 2A) of Embodiment 1, rotation torque is applied to the pair of protrusions 19. The pair of protrusions 19 are provided on the luer portion 10, which is a part that is separate from the lock portion 20 in which the first female threading 21 is provided. Rotation torque is transmitted from the luer portion 10 to the lock portion 20 via the rotation prevention mechanisms made up of the receding portions 16 and the protruding portions 26. Accordingly, in the case where the first female threading 21 and the male threading 925 have been screwed together firmly, if a large amount of rotation torque is applied to the pair of protrusions 19, it is possible for a situation to occur in which instead of the screwing together of the first female threading 21 and the male threading 925 being loosened, the engagement (fitting together) of the receding portions 16 and the protruding portions 26 is released, and the screwing together of the spiral protrusion 14 and the second female threading 22 is loosened. In Embodiment 1, the engagement (fitting together) of the receding portions 16 and the protruding portions 26 needs to be firm in order to prevent such a situation from occurring. However, this reduces the operability of the connection/separation of the luer portion 10 and the lock portion 20.

In Embodiment 3, the rotation prevention mechanisms made up of the receding portions 316 and the protruding portions 326 are not arranged in the path of transmission of rotation torque applied to the male connector 3 during the connection/separation of the male connector 3 and the female connector 920. Accordingly, when separating the male connector 3 and the female connector 920, it is possible to reliably loosen the screwing together of the first female threading 21 and the male threading 925, without loosening the screwing together of the spiral protrusion 14 and the second female threading 22.

For this reason, in Embodiment 3, the rotation prevention mechanisms made up of the receding portions 316 and the protruding portions 326 do not need to transmit a large amount of rotation torque, unlike the rotation prevention mechanisms made up of the receding portions 16 and the protruding portions 26 in Embodiment 1, and thus there is an improvement in the degree of freedom in design. Also, there is an improvement in the operability of the connection/separation of the luer portion 310 and the lock portion 320.

Although the male connector 3 is constituted by two parts, namely the luer portion 310 and the lock portion 320, it has a configuration in which the base end portion 18 of the luer portion 310 and the pair of extension portions 325 of the lock portion 320 can be gripped integrally, and therefore the operability of connection to and separation from the female connector 920 is equivalent to the operability when the male connector 910 constituted by one part is connected to and separated from the female connector 920.

When the lock portion 320 has been attached to the luer portion 310, the extension portions 325 and the protrusions 319 are continuous in the up-down direction as if they were one object (see FIG. 6A). Accordingly, when the base end portion 18 is gripped, even if the extension portions 325 and the protrusions 319 are gripped at the same time, relative rotation force does not act between the luer portion 310 and the lock portion 320. Accordingly, in view of this point as well, the screwing together of the spiral protrusion 14 and the second female threading 22 does not become loosened during the operations for connecting/separating the male connector 3 to/from the female connector 920.

As shown in FIGS. 6B and 6C, when the lock portion 320 has been attached to the luer portion 310, the tubular portion 313 and the small diameter portion 323 are fitted to each other. Since the male tapered face of the tubular portion 313 and the female tapered face of the small diameter portion 323 have the same taper angle and diameter, a liquid-tight seal is formed between the tubular portion 313 and the small diameter portion 323.

The outer circumferential face 12 of the male luer 11 comes into liquid-tight surface contact with the inner circumferential face 922 of the insertion portion 921 of the female connector 920 (FIGS. 12A and 12B). Accordingly, when the male connector 3 and the female connector 920 are in the connected state, there is a low possibility of a nutrient leaking out from between the outer circumferential face 12 of the male luer 11 and the inner circumferential face 922 of the insertion portion 921. However, if the nutrient has been filled up to the edge of the opening of the insertion portion 921 immediately before the male connector 3 and the female connector 920 are connected, there are cases where the nutrient leaks out from the insertion portion 921 when the male luer 11 is inserted into the insertion portion 921. In Embodiment 3, a liquid-tight seal is formed between the tubular portion 313 and the small diameter portion 323, and therefore a leaked nutrient does not flow between the spiral protrusion 14 and the second female threading 22. Accordingly, it is possible to lower the possibility that a nutrient leaks out of the male connector 3 along the lower face 324a of the lock portion body 324 and soils the patient's body or clothes. It is also possible to suppress the attachment of a nutrient to the luer portion 310 (particularly the spiral protrusion 14 that is relatively difficult to clean), which is not easily replaced due to being connected to the tube 8. Furthermore, it is possible to reduce the possibility of a situation occurring in which a nutrient that leaked out from between the luer portion 310 and the lock portion 320 becomes stuck thereto and makes it difficult to separate the luer portion 310 and the lock portion 320.

The protrusions 319 of Embodiment 3 are smaller than the protrusions 19 of Embodiment 1. This is advantageous to reducing the possibility that the patient or the like makes an operation mistake such as a mistaken disassembly to the luer portion 310 and the lock portion 320. On the other hand, there is a possibility of somewhat reducing the operability of the connection/separation of the luer portion 310 and the lock portion 320 when cleaning the male connector 3, for example. In response to this, it is possible to compensate for this reduction in operability by using a jig that engages with the pair of protrusions 319, for example. The following describes an example of such a jig.

Figure 7A:
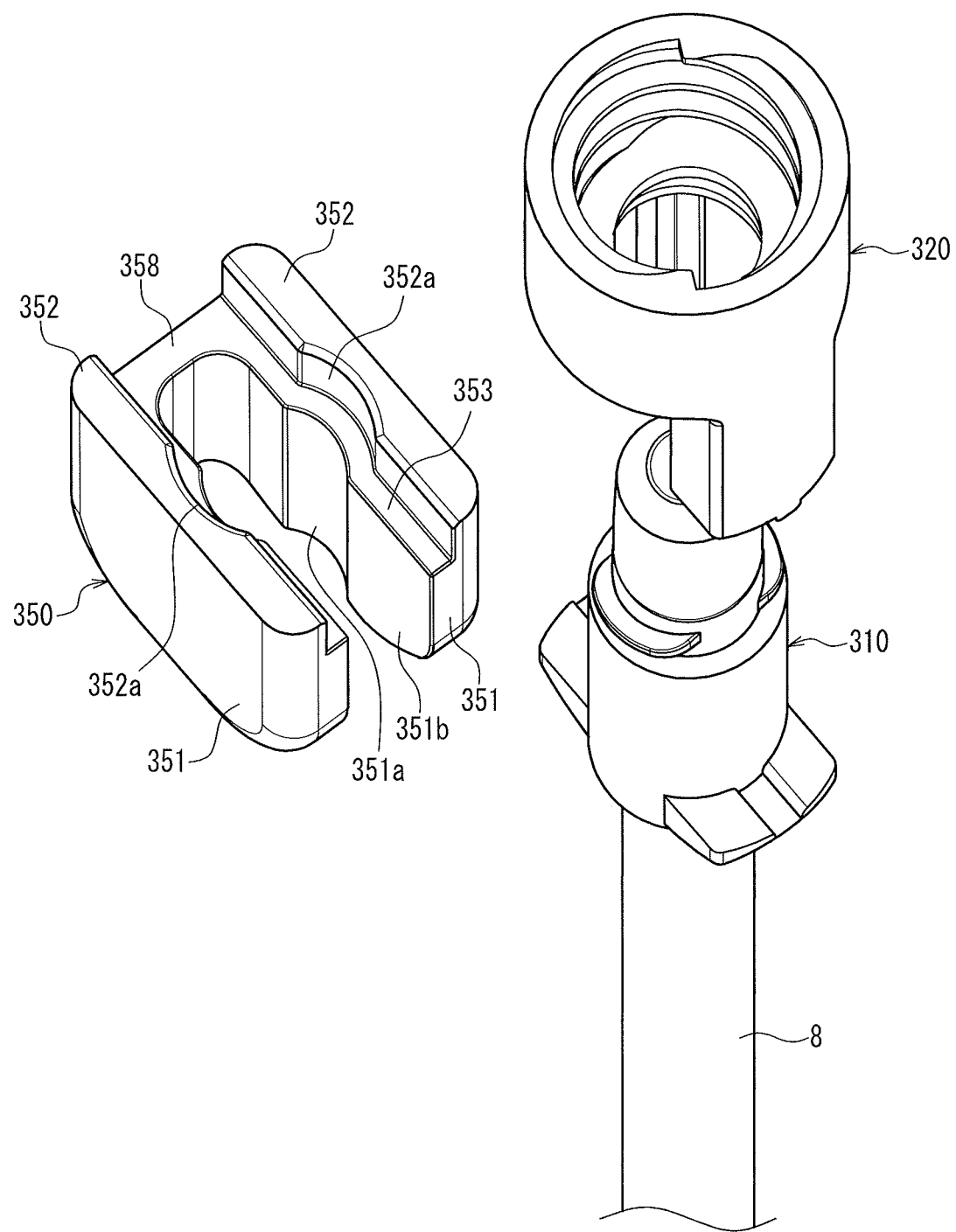
FIG. 7A is a perspective diagram showing one step in a method for assembling the male connector according to Embodiment 3 of the present invention using a jig.

FIG. 7A is an exploded perspective diagram showing a state immediately before the luer portion 310 and the lock portion 320 are connected using a jig 350. The jig 350 approximately has a "U" shape when viewed from above, in which a pair of gripping plates 351 that oppose each other are connected by a connection portion 358. Restriction portions 352 protrude upward from outward portions (portions distant from the opposing gripping plates 351) of the upper faces of the pair of gripping plates 351. Relatively lower portions inward of the restriction portions 352 are holding portions 353.

First receding portions 351a are formed on mutually opposing faces 351b of the pair of gripping plates 351 that are below the holding portions 353, and second receding portions 352a are formed on mutually opposing faces of the pair of restriction portions 352. The mutually opposing first receding portions 351a formed on the faces 351b constitute portions of a common cylindrical face, and the mutually opposing second receding portions 352a formed on the restriction portions 352 also constitute portions of a common cylindrical face. The cylindrical face of the first receding portions 351a and the cylindrical face of the second receding portions 352a are coaxial.

The following describes a method of connecting the luer portion 310 and the lock portion 320 using the jig 350 described above.

As shown in FIG. 7A, the open side of the jig 350 (the side opposite to the connection portion 358) is arranged so as to oppose the tube 8.

Figure 7B:
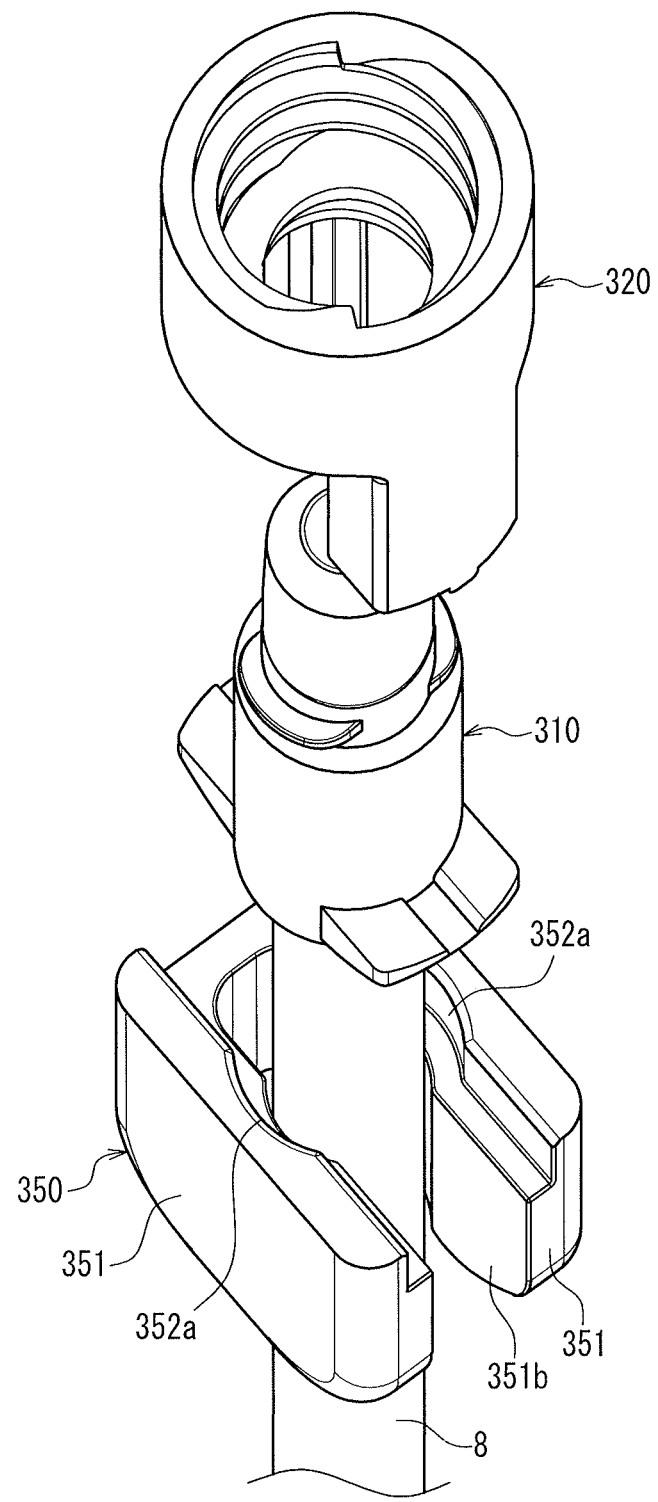
FIG. 7B is a perspective diagram showing one step in the method for assembling the male connector according to Embodiment 3 of the present invention using the jig.

Next, as shown in FIG. 7B, the tube 8 is inserted into the space between the pair of gripping plates 351. The outer diameter of the tube 8 is larger than the gap between the mutually opposing faces 351b of the gripping plates 351, and is the same as or slightly smaller than the diameter of the cylindrical face formed by the mutually opposing first receding portions 351a (see FIG. 7A). Accordingly, the tube 8 undergoes deformation so as to decrease in diameter when passing between the mutually opposing faces 351b. Then, when the tube 8 is fitted between the mutually opposing first receding portions 351a as shown in FIG. 7B, it returns to its initial state.

Figure 7C:
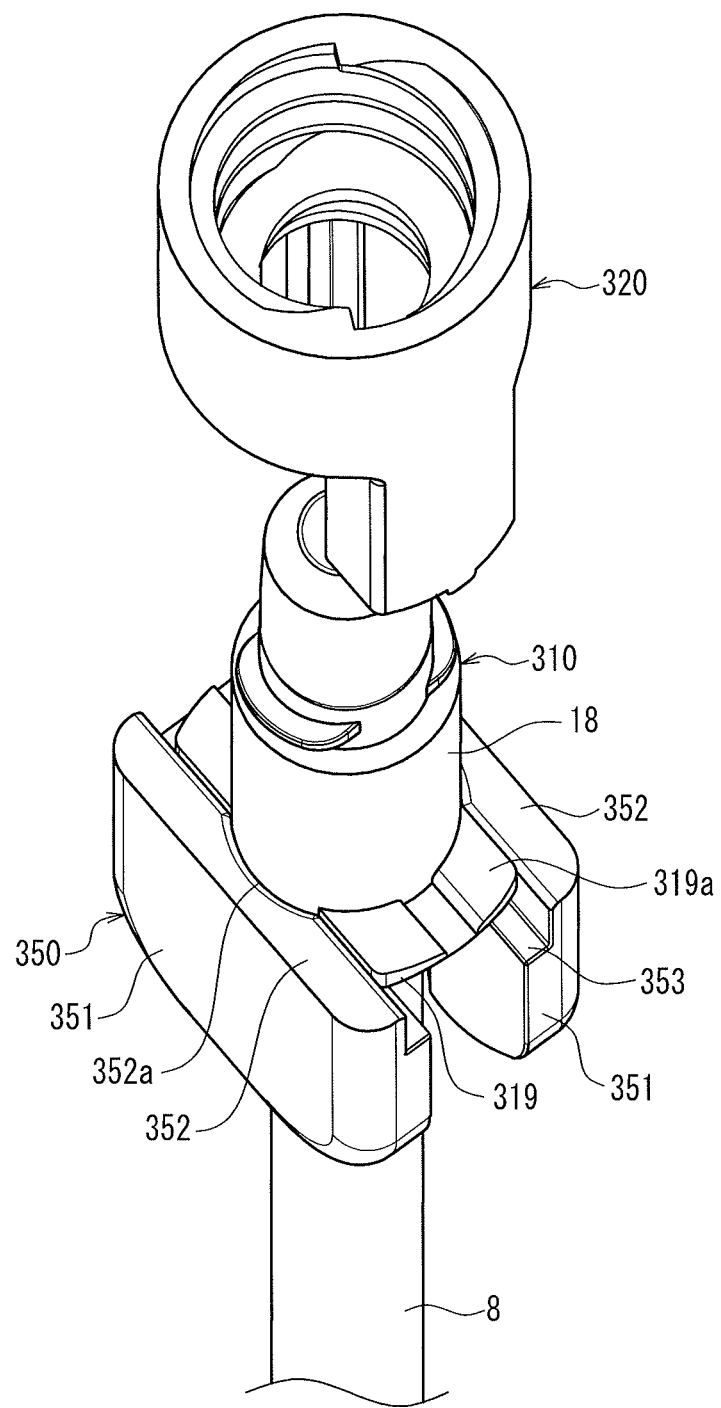
FIG. 7C is a perspective diagram showing one step in the method for assembling the male connector according to Embodiment 3 of the present invention using the jig.

Subsequently, while the tube 8 has been fitted between the mutually opposing first receding portions 351a, the jig 350 is raised. The outer diameter of the base end portion 18 is larger than the diameter of the cylindrical face formed by the mutually opposing first receding portions 351a, and the same as or slightly smaller than the diameter of the cylindrical face formed by the mutually opposing second receding portions 352a. Accordingly, as shown in FIG. 7C, the base end portion 18 is fitted between the mutually opposing second receding portions 352a, and the lower end of the base end portion 18 comes into contact with the holding portions 353. The pair of protrusions 319 protruding from the base end portion 18 are fitted between the pair of restriction portions 352. The upper faces 319a of the protrusions 319 are at a location that is the same as or higher than the upper ends of the restriction portions 352. The luer portion 310 is restricted from moving downward relative to the jig 350, and is restricted from rotating relative to the jig 350.

Figure 7D:
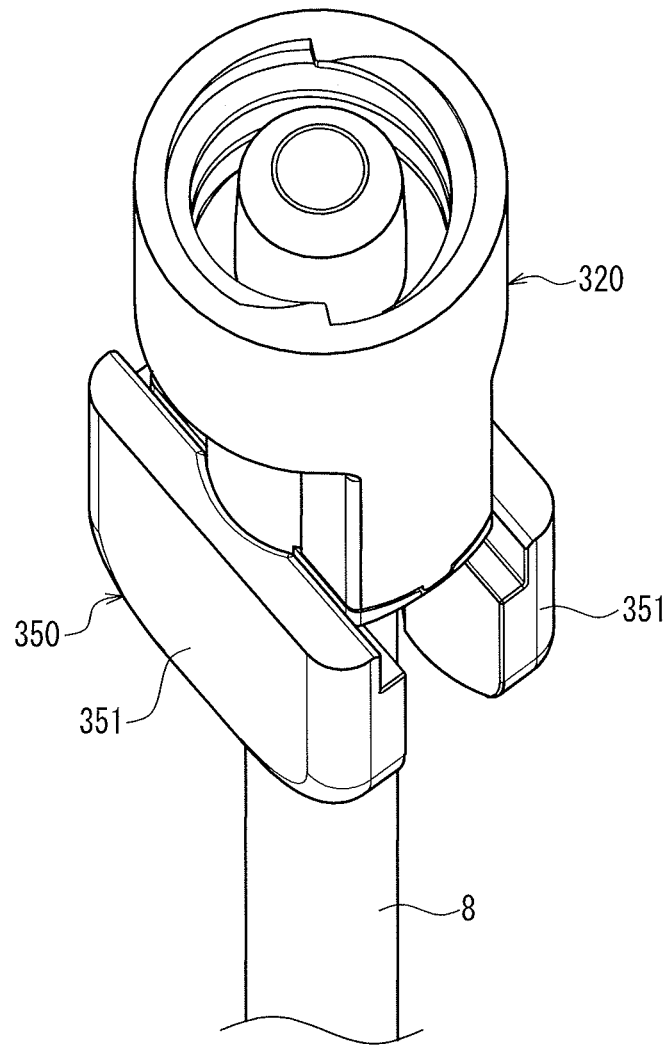
FIG. 7D is a perspective diagram showing one step in the method for assembling the male connector according to Embodiment 3 of the present invention using the jig.

In this state, the lock portion 320 is placed over the luer portion 310, and, similarly to the description given above, the lock portion 320 and the luer portion 310 are rotated in mutually opposite directions, and the lock portion 320 is attached to the luer portion 310 as shown in FIG. 7D.

The separation of the luer portion 310 and the lock portion 320 can be performed by performing the above-described operations in reverse.

When attachment and separation have respectively ended, the jig 350 is separated from the tube 8.

As described above, the jig 350 restricts vertical movement and rotation of the luer portion 310. Accordingly, the luer portion 310 can be held via the jig 350 so as to not fall, and rotation torque can be applied to the luer portion 310 via the jig 350. For this reason, by holding the luer portion 310 via the pair of gripping plates 351 of the jig 350, the lock portion 320 can be easily attached to and separated from the luer portion 310.

The gap between the mutually opposing faces 351b of the pair of gripping plates 351 is smaller than the outer diameter of the tube 8, and therefore once the tube 8 has been inserted between the first receding portions 351a (see FIG. 7B), even if the jig 350 is let go, the jig 350 does not fall away from the tube 8. Accordingly, the operability of attachment and separation improves.

The shape of the jig 350 is not limited to the above-described example. For example, receding portions into which the protrusions 319 are fitted may be formed in the upper faces of the pair of gripping plates 351. In this case, falling and rotation of the luer portion 310 are restricted by fitting the pair of protrusions 319 to the pair of gripping plates 351.

Embodiment 3 is the same as Embodiment 1 with the exception of the content described above. The description of Embodiment 1 applies to Embodiment 3 as well.

Embodiment 4

A male connector 4 of Embodiment 4 is different from the male connector 3 of Embodiment 3 with respect to the positions where the receding portions and the protruding portions that constitute the rotation prevention mechanisms are provided. The male connector 4 of Embodiment 4 will be described with focus on differences from the male connector 3 of Embodiment 3. In the drawings referenced below, elements the same as or corresponding to elements of the male connector 3 of Embodiment 3 are denoted by the same reference signs, and detailed descriptions will not be given for them.

Figure 8A:
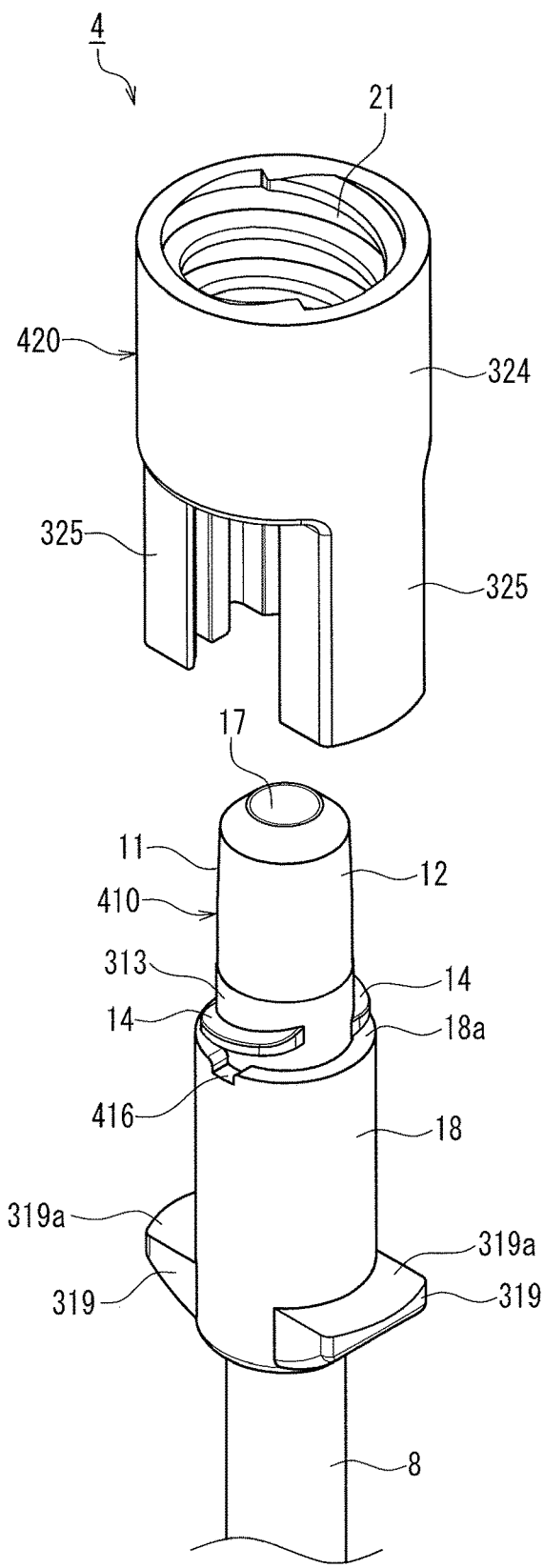
FIG. 8A is an exploded perspective view of a male connector according to Embodiment 4 of the present invention, as viewed from above.
Figure 8B:
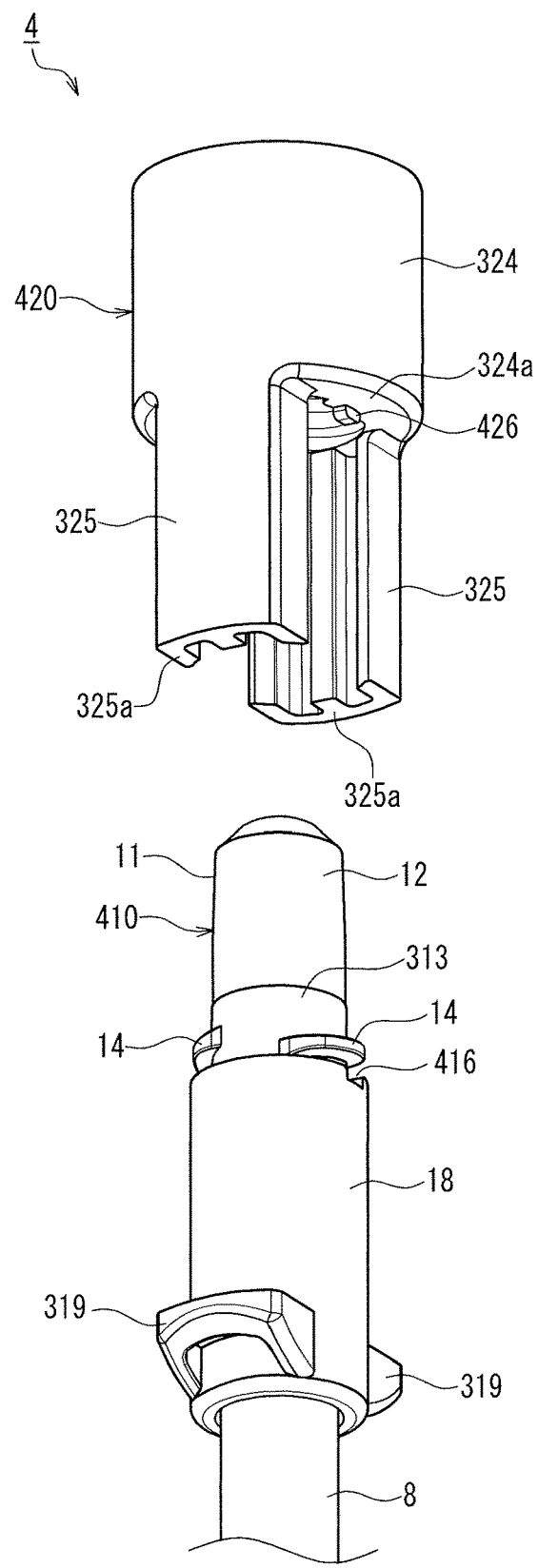
FIG. 8B is an exploded perspective view of the male connector according to Embodiment 4 of the present invention, as viewed from below.
Figure 8C:
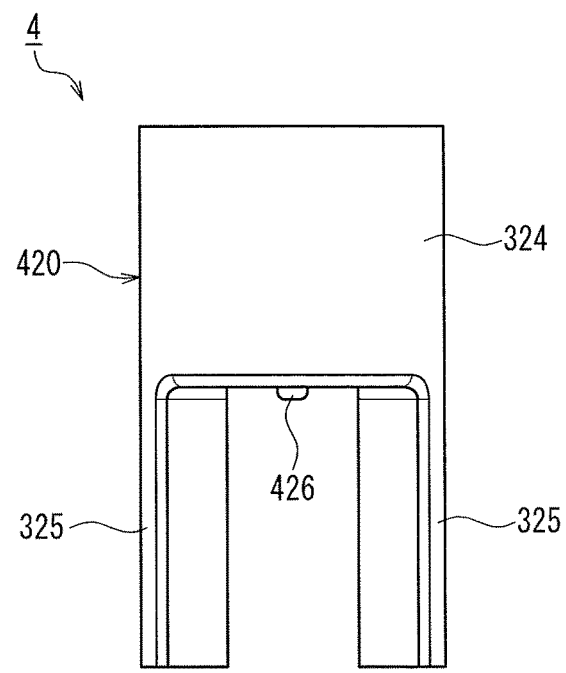
FIG. 8C is an exploded side view of the male connector according to Embodiment 4 of the present invention.
Figure 8C:
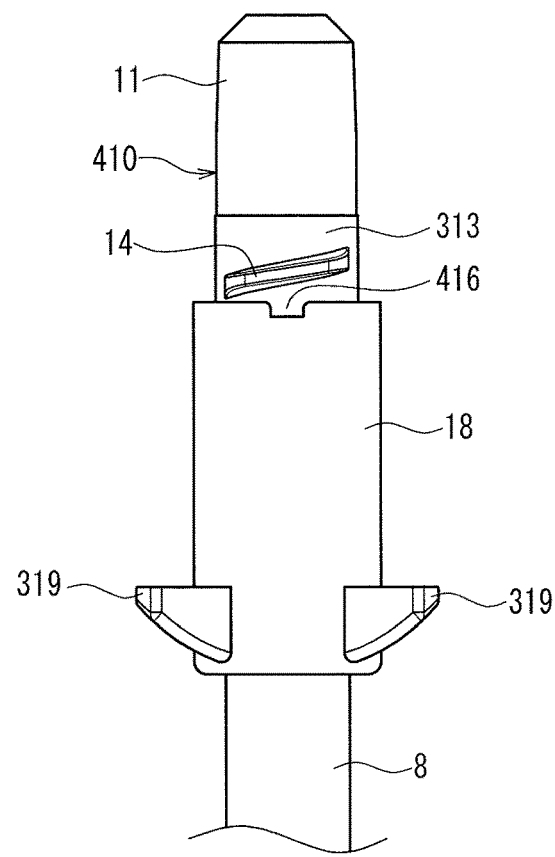
Figure 8D:
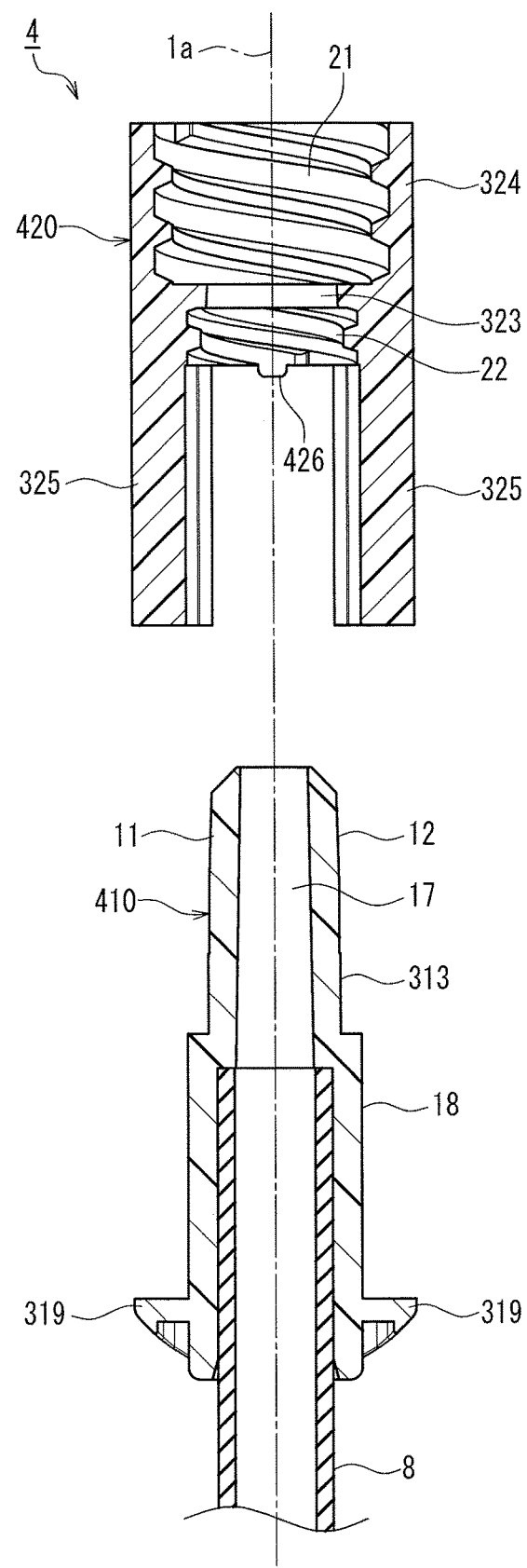
FIG. 8D is an exploded cross-sectional view taken along a plane that includes the central axis of the male connector according to Embodiment 4 of the present invention.

FIG. 8A is an exploded perspective view of the male connector 4 according to Embodiment 4 of the present invention, as viewed from above. FIG. 8B is an exploded perspective view of the male connector 4, as viewed from below. FIG. 8C is an exploded side view of the male connector 4. FIG. 8D is an exploded cross-sectional view taken along a plane that includes the central axis 1a of the male connector 4.

Similarly to the male connector 3 of Embodiment 3, the male connector 4 of Embodiment 4 includes a luer portion 410 and a lock portion 420.

As shown in FIG. 8A, in the luer portion 410, the receding portions 316 (see FIG. 5A) are not formed in the upper faces 319a of the protrusions 319. Instead, a pair of receding portions 416 are formed in the upper face 18a of the base end portion 18, which is formed due to the difference between the outer diameters of the tubular portion 313 and the base end portion 18. The pair of receding portions 416 are in rotation symmetry (two-fold symmetry) about the central axis 1a.

As shown in FIG. 8B, in the lock portion 420, the protruding portions 326 (see FIG. 5B) are not formed on the lower faces 325a of the extension portions 325. Instead, a pair of protruding portions 426 are formed on the lower faces 324a of the lock portion body 324. The pair of protruding portions 426 are in rotation symmetry (two-fold symmetry) about the central axis 1a.

With the exception of the above, the luer portion 410 and the lock portion 420 are the same as the luer portion 310 and the lock portion 320 of Embodiment 3.

In Embodiment 4 as well, the lock portion 420 can be repeatedly attached to and detached from the luer portion 410. The attachment of the lock portion 420 to the luer portion 410 is approximately the same as in Embodiment 3. The male luer 11 is inserted into the lock portion 420 from the lower side thereof, and the lock portion 420 is rotated relative to the luer portion 410 so as to screw the spiral protrusion 14 and the second female threading 22 together. The protruding portions 426 of the lock portion 420 are fitted into the receding portions 416 of the luer portion 410, and, at the same time, the lower faces 325a of the extension portions 325 and the upper faces 319a of the protrusions 319 oppose each other. When the pair of protruding portions 426 are fitted into the pair of receding portions 416, the rotation torque for rotating the lock portion 420 changes, and the operator can feel that change as a clicking sensation through their fingers.

Figure 9A:
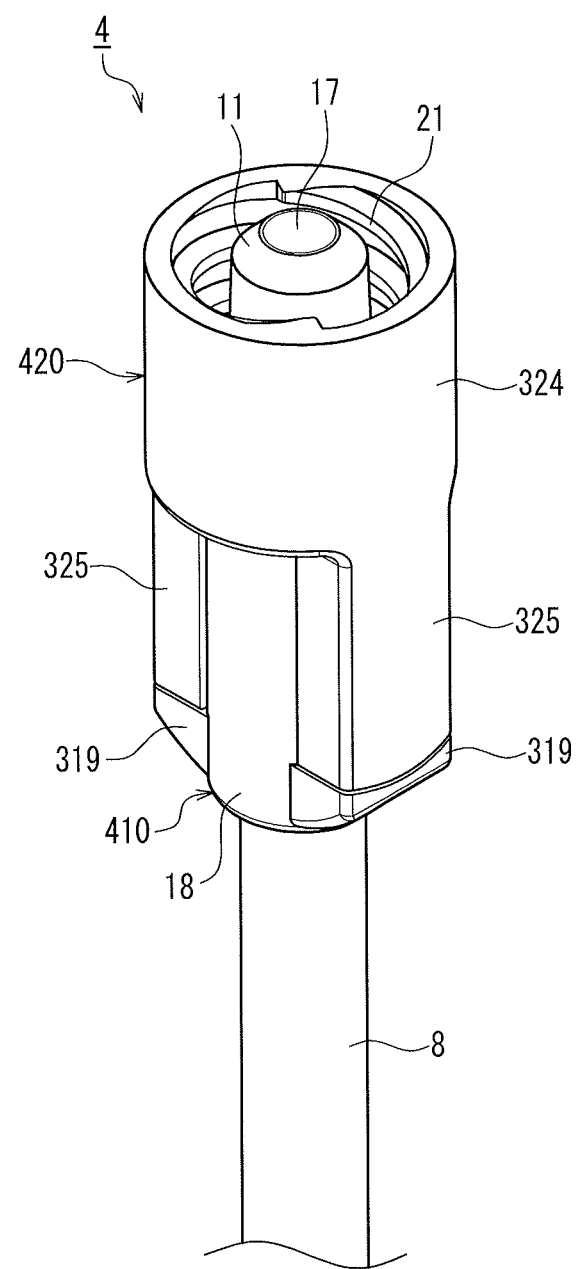
FIG. 9A is a perspective view of the male connector according to Embodiment 4 of the present invention, as viewed from above.
Figure 9B:
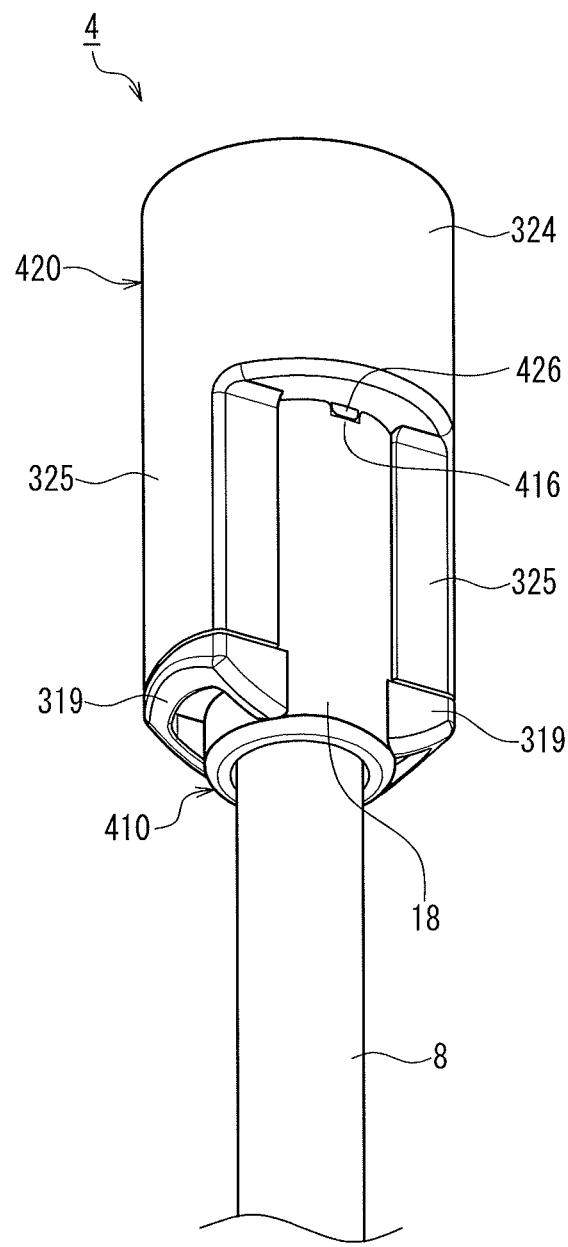
FIG. 9B is a perspective view of the male connector according to Embodiment 4 of the present invention, as viewed from below.
Figure 9C:
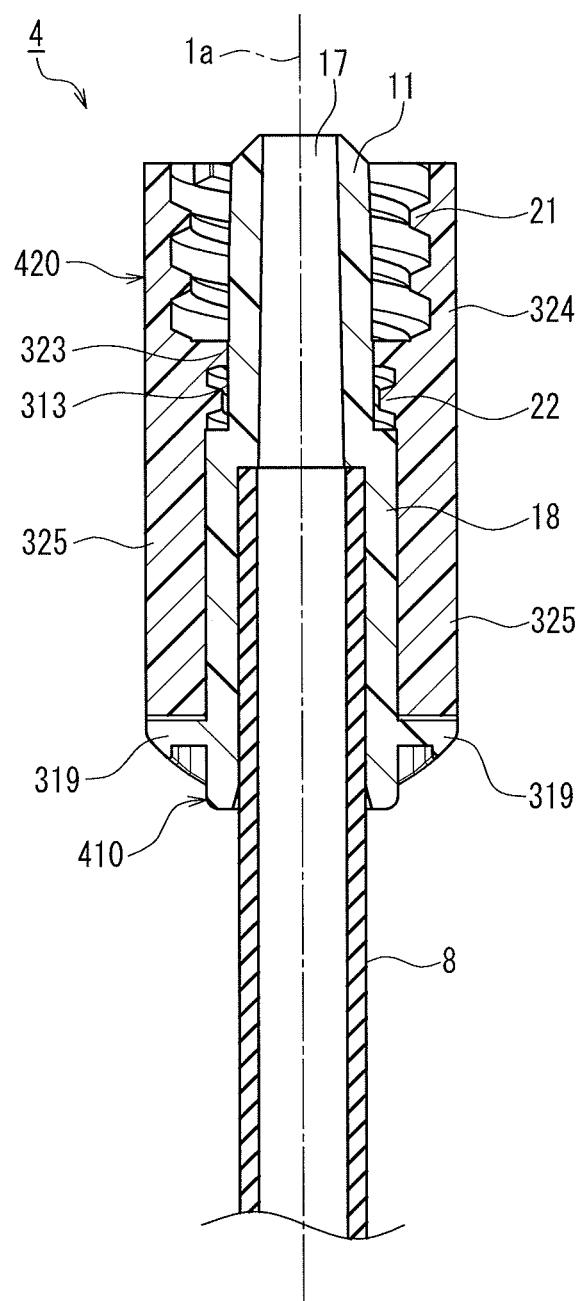
FIG. 9C is a cross-sectional view taken along a plane that includes the central axis of the male connector according to Embodiment 4 of the present invention.
Figure 9D:
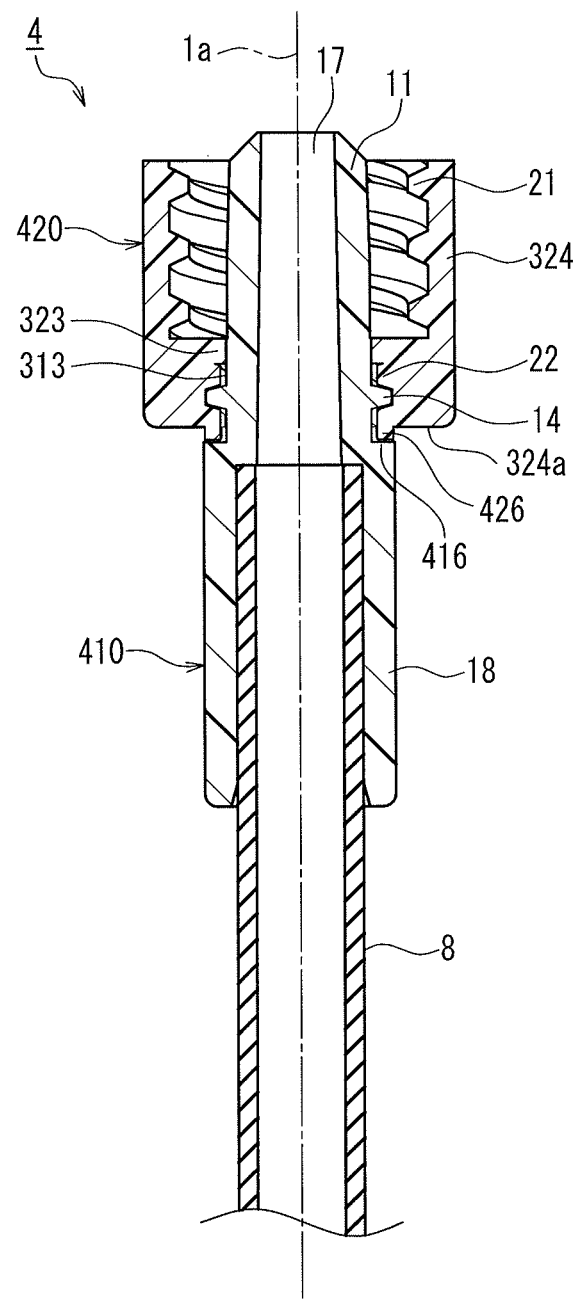
FIG. 9D is a cross-sectional view taken along a different plane that includes the central axis of the male connector according to Embodiment 4 of the present invention.

Thus, the lock portion 420 is attached to the luer portion 410, as shown in FIGS. 9A to 9D. FIG. 9A is a perspective view of the male connector 4 with the lock portion 420 attached to the luer portion 410, as viewed from above. FIG. 9B is an exploded perspective view of the male connector 4, as viewed from below. FIG. 9C is a cross-sectional view of the male connector 4 taken along a plane that includes the central axis 1a and the extension portions 325. FIG. 9D is a cross-sectional view of the male connector 4 taken along a different plane that includes the central axis 1a. The cross-section in FIG. 9D is orthogonal to the cross-section in FIG. 9C.

As shown in FIG. 9B, the pair of extension portions 325 of the lock portion 420 oppose the base end portion 18 of the luer portion 410 in the radial direction, and are arranged on respective sides of the base end portion 18. The extension portions 325 and the protrusions 319 oppose each other in the up-down direction, and the exposed outer faces of the extension portions 325 constitute faces that are approximately continuous with the outer faces of the protrusions 319. The protruding portions 426 are fitted into the receding portions 416.

Similarly to Embodiment 3, the luer portion 410 and lock portion 420 can be separated by rotating the lock portion 420 relative to the luer portion 410, in the direction opposite to that during attachment. In order to begin rotation, the protruding portions 426 and the receding portions 416 need to be disengaged, and a somewhat large amount of rotation torque needs to be applied for disengagement. After the protruding portions 426 have escaped the receding portions 416, the lock portion 420 can be easily rotated relative to the luer portion 410 with a small rotation torque.

The attachment and detachment of the luer portion 410 and the lock portion 420 can be repeatedly performed any number of times.

The method of use and effects of the male connector 4 of Embodiment 4 are the same as those of the male connector 3 of Embodiment 3. The jig 350 (see FIGS. 7A to 7D) described in Embodiment 3 can be used in the assembly and disassembly of the male connector 4.

In Embodiment 4, the protruding portions 426 are formed on the lower face 324a of the lock portion body 324, and therefore there is a lower possibility of the protruding portions becoming damaged or worn due to colliding with another member or the like, compared to Embodiment 3 in which the protruding portions 326 are formed on the lower faces 325a of the extension portions 325 (see FIG. 5B).

Embodiment 4 is the same as Embodiment 3 with the exception of the content described above. The description of Embodiment 3 applies to Embodiment 4 as well.

Embodiments 1 to 4 described above are merely illustrative examples. The present invention is not limited to Embodiments 1 to 4 described above, and can be modified as necessary.

In the male connectors 3 and 4 of Embodiments 3 and 4, a liquid-tight seal is formed between the tubular portion 313 and the small diameter portion 323. A similar seal may be provided in the male connectors 1 and 2 of Embodiments 1 and 2. For example, in Embodiment 1, a liquid-tight seal can be formed between the tubular portion 13 of the luer portion 10 and the small diameter portion 23 (see FIG. 1D) between the first female threading 21 and the second female threading 22 of the lock portion 20 by respectively forming thereon a male tapered face and a female tapered face that can be fitted to each other and are similar to the tubular portion 313 and the small diameter portion 323 of Embodiments 3 and 4. As another example, in Embodiment 2, a liquid-tight seal can be formed between the tubular portion 213 of the luer portion 210 and the cylindrical face 222 of the lock portion 220 by respectively forming thereon a male tapered face and a female tapered face that can be fitted to each other and are similar to the tubular portion 313 and the small diameter portion 323 of Embodiments 3 and 4. In Embodiments 3 and 4, the seal is formed by a male tapered face and a female tapered face that can be fitted to each other, but the present invention is not limited to this. For example, a liquid-tight seal may be formed by two cylindrical faces that can be fitted to each other. A liquid-tight seal may be formed by attaching an O-ring to either the luer portion or the lock portion, and bringing the O-ring into close contact with the other one.

The position where the liquid-tight seal is formed is not limited to the positions in Embodiments 3 and 4, and need only be a position lower than (on the tube 8 side of) the male luer 11. For example, the seal may be formed lower than the spiral protrusion 14 and the second female threading 22. The seal does not need to be formed at a position where the luer portion and the lock portion oppose each other in the radial direction, and it may be formed at a position where the luer portion and the lock portion oppose each other in the up-down direction, for example.

The male connector of the present invention may be a male connector in which a liquid-tight seal is not formed between the luer portion and the lock portion.

A protrusion may be provided on the lock portion 20, 220, 320, 420 as well so as to enable firmly gripping the lock portion 20, 220, 320, 420 when the lock portion 20, 220, 320, 420 is attached to or detached from the luer portion 10, 210, 310, 410. There are no limitations on the shape of the protrusion, and, for example, a pair of protrusions shaped as thin plates that are similar to the protrusions 19 provided on the luer portion 10, 210 can be provided on the outer circumferential face of the lock portion 20, 220, 320, 420, so as to extend along a plane that includes the central axis 1a.

Alternatively, a protrusion (convex portion) or recession (concave portion) capable of engaging with a jig may be provided on the lock portion 20, 220, 320, 420. For example, multiple protrusions or multiple recessions can be provided on the upper face of the lock portion 20, 320, 420 (face on the side opposite to the lower face 20a, 324a) of Embodiment 1, 3, 4. Multiple receding portions or multiple protruding portions that engage with the aforementioned protrusions or recessions are provided on one face of a disc-shaped jig whose outer diameter is larger than the outer diameter of the lock portion 20, 320, 420. When the lock portion 20, 320, 420 is attached to or detached from the luer portion 10, 310, 410, the aforementioned jig is attached to the lock portion 20, 320, 420, and rotation torque is applied to the lock portion 20, 320, 420 via the jig. Accordingly, the operations of attachment and detachment of the lock portion 20, 320, 420 are made easier.

The shape and number of protrusions 19, 319 provided on the luer portion 10, 210, 310, 410 are not limited to those in the above-described embodiments. The protrusions 19 may be omitted in Embodiments 1 and 2, and the protrusions 319 may be omitted in Embodiment 4.

In the male connectors 1, 3, and 4 of Embodiments 1, 3, and 4, the spiral protrusion 14 of the luer portion 10 may be a continuous thread with a thread ridge that is continuous in the circumferential direction (i.e., general male threading) instead of being a discontinuous thread whose thread ridge is divided in the circumferential direction.

The number of protruding portions 26, 226, 326, 426 and receding portions 16, 216, 316, 416 that constitute the rotation prevention mechanisms is not limited to being two, and may be one or a number greater than or equal to three. A configuration is possible in which the protruding portions are formed on the luer portion, and the receding portions are formed in the lock portion.

The shapes of the protruding portions 26, 226, 326, 426 and the receding portions 16, 216, 316, 416 that constitute the rotation prevention mechanisms are not limited to the shapes in the above-described embodiments.

Although the shapes of the protruding portions 26, 226, 326, 426 and the receding portions 16, 216, 316, 416 in a view along the radial direction are all rectangular shapes in the above-described embodiments, the present invention is not limited to this, and any shape can be applied. For example, a protruding portion 826 and a receding portion 816 shown in FIG. 10A may be applied. The protruding portion 826 includes a top face (most protruding face) 826a that is parallel with the horizontal direction, an inclined face 826b that is inclined relative to the horizontal direction and is adjacent to the top face 826a on one side in the circumferential direction, and a vertical face 826c that is parallel with the up-down direction and is adjacent to the top face 826a on the other side in the circumferential direction. The receding portion 816 includes a bottom face 816a, an inclined face 816b, and a vertical face 816c that respectively correspond to the top face 826a, the inclined face 826b, and the vertical face 826c of the protruding portion 826. An arrow A indicates the direction of rotation of the lock portion 820 relative to the luer portion 810 when the lock portion 820 provided with the protruding portion 826 is mounted to the luer portion 810 provided with the receding portion 816. The protruding portion 826 includes the inclined face 826b on the forward side of the arrow A, and therefore the protruding portion 826 and the receding portion 816 can be engaged (fitted together) relatively easily. For example, in the case where the protruding portion 826 and the receding portion 816 are respectively provided on the lower faces 325a of the extension portions 325 and the upper faces 319a of the protrusions 319 in Embodiment 3, even when the inclined faces 826b of the protruding portions 826 collide with the edges of the protrusions 319 (edges 810e in FIG. 10A), the protruding portions 826 can easily ride over the edges 810e.

Figure 10A:
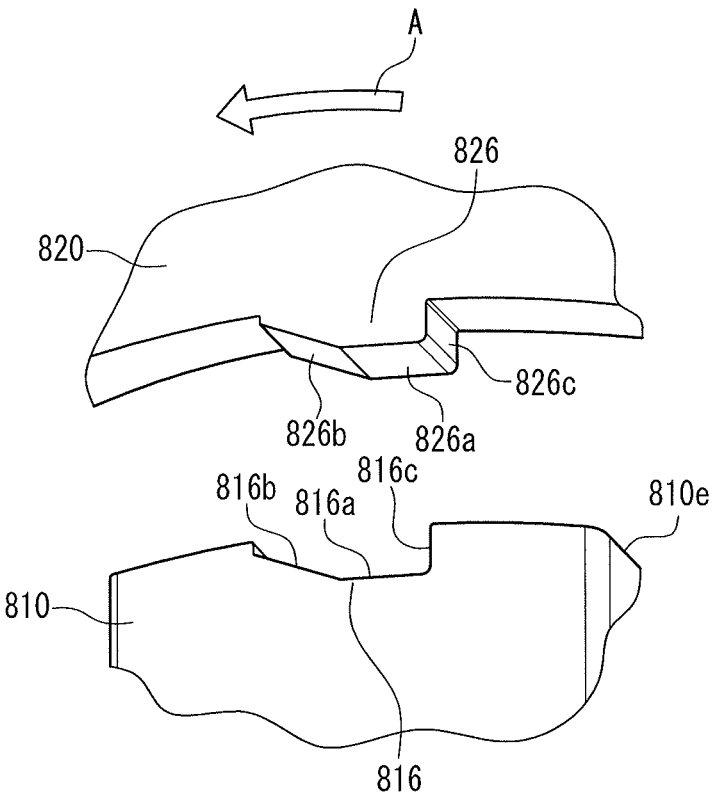
FIG. 10A is a perspective diagram showing another example of a protruding portion and a receding portion that constitute rotation prevention mechanisms
Figure 10B:
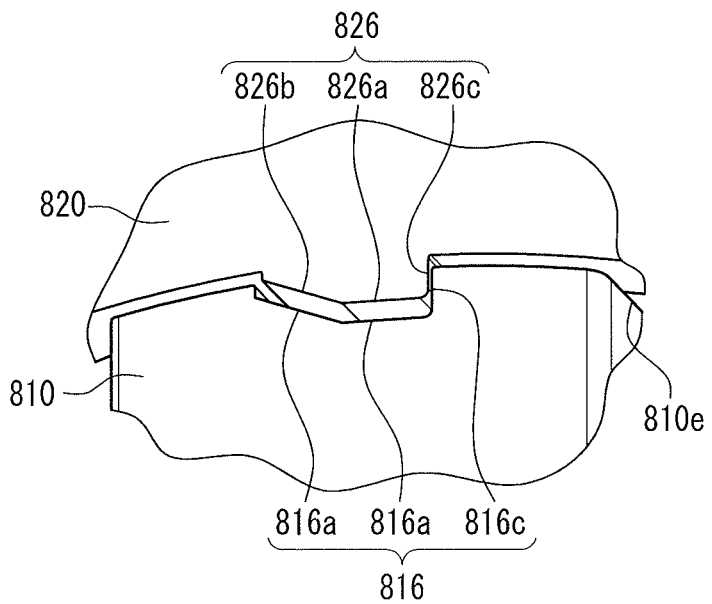
FIG. 10B is a perspective diagram showing a state in which the protruding portion and the receding portion shown in FIG. 10A are fitted together.

FIG. 10B is a perspective diagram showing a state in which the lock portion 820 has been attached to the luer portion 810, and the protruding portion 826 and the receding portion 816 have been engaged (fitted together). The top face 826a, the inclined face 826b, and the vertical face 826c of the protruding portion 826 respectively oppose the bottom face 816a, the inclined face 816b, and the vertical face 816c of the receding portion 816. The vertical face 826c and the vertical face 816c oppose each other in the circumferential direction, and therefore a relatively large amount of force is needed in order to release the engagement (fitting together) of the protruding portion 826 and the receding portion 816.

Due to the rotation prevention mechanisms being constituted by the protruding portion 826 and the receding portion 816 that are asymmetrical in the circumferential direction in this way, it is possible to easily realize a male connector that makes assembly relatively easy and makes disassembly relatively difficult. Accordingly, it is possible to reduce the possibility of the luer portion and the lock portion becoming separated unintentionally.

In FIGS. 10A and 10B, the faces that constitute the protruding portion 826 and the receding portion 816 do not need to be flat faces, and may be curved faces. A configuration is possible in which the protruding portion 826 and the receding portion 816 are not provided with the top face 826a and the bottom face 816a, and instead are respectively a triangular protruding portion in which the inclined face 826b and the vertical face 826c are adjacent to each other, and a triangular receding portion in which the inclined face 816b and the vertical face 816c are adjacent to each other. The vertical faces 826c and 816c may be changed to inclined faces that are inclined relative to the horizontal direction.

The rotation prevention mechanisms that engage in the circumferential direction are not limited to being constituted by the protruding portions 26, 326, 426 and the receding portions 16, 316, 416. For example, they may be constituted by two protruding portions respectively formed on two faces that oppose each other. In this case, the two protruding portions engage with each other by one of the protruding portions riding over the other protruding portion, and thus the rotation prevention mechanisms enter the locked state. The shapes of the two protruding portions when viewed along the radial direction may be rectangular shapes similar to those of the protruding portions 26, 326, 426, or may be shapes that are asymmetrical in the circumferential direction with an inclined face on the forward side and a vertical face on the rear side in terms of the direction of relative movement during engagement, similarly to the protruding portion 826 shown in FIG. 10A.

The separation prevention mechanisms may have a configuration other than the screwing structures constituted by the spiral protrusion 14 and the second female threading 22. For example, they may be configured by engaging structures that can engage with each other (e.g., one protruding portion and another protruding portion, or a protruding portion and a receding portion).

In Embodiments 3 and 4, the number of extension portions 325 provided on the lock portion is not limited to two, and one or a number greater than or equal to three may be provided. In the case of two or more extension portions, it is preferable that the extension portions 325 are arranged at equiangular intervals relative to the central axis 1a. Providing two extension portions is preferable from the viewpoint of the operability of connection to and separation from the female connector 920, and the operability of the cleaning of the lock portion (the female threading 21 and 22 in particular). The number of protrusions 319 can be changed according to the number of extension portions 325.

Alternatively, the extension portion may have a tubular shape for covering the outer circumferential face of the base end portion 18 in the circumferential direction. In this case, when the lock portion is attached to the luer portion, the protrusions 319 are exposed below the tubular extension portion. Protrusions (e.g., protrusion similar to the protrusions 19 of Embodiments 1 and 2) or unevenness for preventing slipping may be formed on the outer circumferential face of the extension portion in order to make it possible to easily apply rotation torque to the luer portion.

Besides the description given above, the configurations described in the embodiments and modified configurations thereof can be applied to other embodiments.

In Embodiments 1 to 4 described above, the male connectors 1 to 4 are attached to the upstream end of a so-called "tube-type" PEG catheter, which is a catheter that is inserted into a patient and has a long portion extending outside of the patient's body. However, the male connector of the present invention can also be attached to the upstream end of a tube that is connected to a so-called "button-type" PEG catheter, which is a catheter that substantially does not extend outside of the patient's body. Furthermore, the male connector of the present invention can also be attached to the upstream end of a transnasal catheter. The male connector of the present invention can be provided at the upstream end of any tube through which an enteral nutrient flows.

INDUSTRIAL APPLICABILITY

The present invention is broadly applicable as a male connector provided at the upstream end of a tube used in enteral feeding. This tube may be a catheter that is indwelled in a patient, as with a PEG catheter or a transnasal catheter, or may be a tube that is connected to such a catheter. Among such catheters, the male connector of the present invention can be preferably used as a male connector provided at the upstream end of a PEG catheter that is indwelled in a patient.

DESCRIPTION OF REFERENCE NUMERALS 1, 2, 3, 4 Male connector
8 Tube
10, 210, 310, 410 Luer portion
11 Male luer
14 Spiral protrusion (screwing structure)
16, 216, 316, 416, 816 Receding portion (rotation prevention mechanism)
17 Channel
18 Base end portion
19, 319 Protrusion
20, 220, 320, 420 Lock portion
21 Female threading (first female threading)
22 Second female threading (screwing structure)
26, 226, 326, 426, 826 Protruding portion (rotation prevention mechanism)
313 Tubular portion (male tapered face for forming a seal)
323 Small diameter portion (female tapered face for forming a seal)
325 Extension portion
350 Jig
816b, 826b Inclined face
816c, 826c Vertical face
920 Female connector
921 Insertion portion
925 Male threading

The invention claimed is:

1. A male connector to be provided at an upstream end of a tube used in enteral feeding, the male connector comprising:

a luer portion; and a lock portion that is removably attached to the luer portion, wherein the luer portion includes a base end portion suitable to be connected to the tube and a tubular male luer that is provided on the base end portion and in which a channel in communication with the tube is formed, the lock portion includes a lock portion body and two or more bar-shaped extension portions, and the lock portion body has a hollow tubular shape and is open at two ends and includes female threading that opposes the male luer on an inner circumferential face of the lock portion body, and the bar-shaped extension portions are formed integrally with the lock portion body and extend parallel to a lengthwise direction of the luer portion from an end of the lock portion body, when the lock portion is attached to the luer portion, the male luer is inserted into the lock portion body, and the bar-shaped extension portions of the lock portion are arranged radially outward relative to the base end portion of the luer portion so that the bar-shaped extension portions cover part of an outer circumferential face of the base end portion of the luer portion and expose a remaining part thereof, rotation prevention mechanisms that engage with one another are provided on the luer portion and the lock portion such that the lock portion does not rotate relative to the luer portion and a male tapered face formed on the luer portion and a female tapered face formed on the lock portion come into direct contact with each other and fit together such that a liquid-tight seal is formed between the luer portion and the lock portion at a position on a tube side relative to the male luer.

2. The male connector according to claim 1, wherein the luer portion is made of a harder material than the lock portion.

3. The male connector according to claim 1, wherein the rotation prevention mechanisms include a protruding portion provided on the lock portion and a receding portion that is provided in the luer portion, the protruding portion being fitted into the receding portion.

4. The male connector according to claim 1,
wherein the rotation prevention mechanisms include a protruding portion formed on one of the lock portion and the luer portion, and a receding portion formed on another one of the lock portion and the luer portion,
the protruding portion includes an inclined face on one side in a circumferential direction, and includes a vertical face on another side in the circumferential direction, and
the receding portion includes an inclined face and a vertical face that respectively oppose the inclined face and the vertical face of the protruding portion when the protruding portion is fitted into the receding portion.

5. The male connector according to claim 1,
wherein the male connector can be connected to a female connector that includes an insertion portion for insertion of the male luer and male threading that is to be screwed together with the female threading, and
the rotation prevention mechanisms are configured such that when the luer portion and the female connector are rotated in mutually opposite directions in order to separate the male connector and the female connector that are connected to each other, screwing together of the female threading and the male threading is loosened, without the lock portion rotating relative to the luer portion.

6. The male connector according to claim 1, wherein separation prevention mechanisms that engage with one another are provided on the luer portion and the lock portion such that the luer portion and the lock portion do not become separated along a lengthwise direction of the male luer.

7. The male connector according to claim 6, wherein the separation prevention mechanisms include screwing structures.

8. The male connector according to claim 1,
wherein the bar-shaped extension portions are configured such that rotation torque can be applied to the male connector via the bar-shaped extension portions.

9. The male connector according to claim 1, wherein the bar-shaped extension portions are arranged so as to protrude outward from the outer circumferential face of the base end portion.

10. The male connector according to claim 1, wherein at least one of the luer portion and the lock portion includes a protrusion or recession for facilitating attachment and detachment of the lock portion to and from the luer portion.

11. The male connector according to claim 10,
further comprising a jig configured so as to engage with the protrusion or recession,
wherein the jig is configured such that rotation torque can be applied to the luer portion or the lock portion via the jig.

12. The male connector according to claim 1, wherein the rotation prevention mechanisms are provided on the outer circumferential face of the base end portion and end faces of the bar-shaped extension portions.

\* \* \* \* \*